United States Patent [19]
Bellon

[11] Patent Number: 5,464,515
[45] Date of Patent: Nov. 7, 1995

[54] APPARATUS FOR THE APPLICATION OF BIOLOGICAL SAMPLES TO AN ELECTROPHORETIC SLAB SUPPORT

[75] Inventor: Franck Bellon, Longjumeau, France

[73] Assignee: Sebia, A Corp. of France, Issy Les Moulineaux, France

[21] Appl. No.: 72,866

[22] Filed: Jun. 4, 1993

Related U.S. Application Data

[63] Continuation of Ser. No. 811,174, Dec. 19, 1991, abandoned.

[30] Foreign Application Priority Data

Jan. 4, 1991 [FR] France ..................... 91 00092

[51] Int. Cl.⁶ ................. G01N 27/26; G01N 27/447
[52] U.S. Cl. .................... 204/182.8; 204/180.1; 204/299 R
[58] Field of Search .................. 204/299 R, 180.1, 204/182.8

[56]  References Cited

U.S. PATENT DOCUMENTS

| | | | |
|---|---|---|---|
| 3,317,418 | 5/1967 | Zec | 204/299 R |
| 3,616,387 | 12/1974 | Siebert et al. | 204/182.8 |
| 3,839,183 | 10/1974 | Klein et al. | 204/299 R |
| 3,855,846 | 12/1974 | Forget et al. | 118/506 X |
| 3,863,599 | 2/1975 | Kohn | 118/256 |
| 3,928,203 | 12/1975 | Kremer | 210/198.3 |
| 3,930,973 | 1/1976 | Nerenberg . | |
| 4,004,548 | 1/1977 | Smola et al. | 204/299 RX |
| 4,096,825 | 6/1978 | Golias et al. | 118/221 |
| 4,214,973 | 7/1980 | Nakamura | 204/299 R |
| 4,272,381 | 6/1981 | Kremer et al. | 210/658 |
| 4,334,879 | 6/1982 | Fujimori | 422/100 X |
| 4,351,800 | 9/1982 | Kopp et al. | 422/100 X |
| 4,696,187 | 9/1987 | Kopp et al. | 73/61.54 |
| 4,812,241 | 3/1989 | Shafer | 210/658 |

FOREIGN PATENT DOCUMENTS

| | | |
|---|---|---|
| 2347674 | 11/1977 | France . |
| 1446125 | 8/1976 | United Kingdom . |

Primary Examiner—John Niebling
Assistant Examiner—John S. Starsiak, Jr.
Attorney, Agent, or Firm—Merchant, Gould, Smith, Edell, Welter & Schmidt

[57]  ABSTRACT

The object of the invention is an apparatus for the application of biological samples, in particular to an electrophoresis gel, comprising:
—one or more planar elements, made of porous material, on which a biological sample is capable of being loaded, these planar elements resting in particular on the edge of a porous planar membrane, joint to the porous membrane and lying in an extention of the plane of the latter, and projecting with respect to the porous membrane, —these elements being designated hereafter as "projecting elements"—, the part of the projecting elements not bound to the porous membrane having a free end,
the above-mentioned projecting elements being such that they all have at least one point capable of being placed in contact with the planar surface of an electrophoretic slab support so that one or more biological samples can be loaded onto the said slab support, each biological sample being loaded beforehand on an element of the projecting elements, these different points being capable of being simultaneously placed in contact with the surface of the said slab support as a result of an alignment, when the above-mentioned porous membrane or the above-mentioned stiffening devices are arranged in an inclined or perpendicular plane with respect to the surface of the above-mentioned slab support.

25 Claims, 5 Drawing Sheets

APPARATUS FOR THE APPLICATION OF BIOLOGICAL SAMPLES TO AN ELECTROPHORETIC SLAB SUPPORT

This is a continuation of application Ser. No. 07/811174, filed Dec. 19, 1991, now abandoned.

The object of the invention is an apparatus for the application of biological samples to an electrophoretic slab support and, advantageously to an electrophoresis gel.

The purpose of the procedures of zone electrophoresis on agarose gel is to fractionate the protein constituents of a biological sample such as serum, urine, cerebro-spinal fluid, etc, by subjecting them to the action of an electric field in a gel medium containing a buffer solution. At a specified, usually basic pH the proteins, which are amphoteric molecules, ionize and are separated according to their respective charges. The fineness of the bands obtained after electrophoresis and hence the resolving power of the procedure depend mainly on the fineness of loading.

In fact, even though in isoelectric focussing, in isotachophoresis or in acrylamide gradient electrophoresis or even in acrylamide gel electrophoresis (by the use of a "stacking gel"), it is possible to obtain a focussing of the fractions by the electrophoresis itself, in zone electrophoresis, for example on agarose gel alone, a very fine loading makes it possible to produce highly focussed fractions.

In order to perform the loading for the purpose of electrophoresis, it is possible to use combs made of plastic material, the teeth of which contain a groove which makes it possible to recover a drop of a biological sample of a volume of about 0.3 to 2 $\mu$l but, on the one hand, the drop is of a dimension such that it usually does not allow a sufficiently fine loading and, on the other, depending on the type of analysis, it is sometimes necessary to carry out a prior dilution of the sample to be analysed, in order not to load too large amounts of sample.

In order to perform loading for the purpose of electrophoresis, it is also possible to use a loading mask with fine slots (about 0.3 to about 0.5 mm) which make it possible to produce good focussing of the loading which is necessary for a satisfactory image. Nonetheless, the use of this mask with loading of samples through the slots is difficult to automate. Moreover, the "automatic" applicators presently available do not enable a fineness of loading to be obtained equivalent to that produced with manual loading performed through the fine slots of the mask.

Furthermore, on account of the relatively large size of the drops, quite wide bands are obtained which makes the separation of the proteins difficult.

In the case of agarose gel, it is also possible to use moulded gels containing wells and, in this case, the syringe which is used to load the sample must be directed very carefully into the well. Loading is usually done successfully if the size of the wells is sufficiently large. Thus, in the case of a well of width greater than or equal to about 1 mm, the apparatus can be automated but the resolution is inadequate. If the size of the wells is sufficiently small to give good resolution, then the apparatus can not be automated.

The object of the invention is to find a solution to these disadvantages by suggesting an apparatus for the application of biological samples which, on the one hand, makes it possible to obtain a fineness of loading sufficient to give high resolution and, on the other, can be automated and which ultimately enables variable amounts of sample to be loaded (quite considerable amounts of sample which can be varied as desired).

The object of the invention is also to provide an apparatus for the application of biological samples at a moderate price.

The object of the invention is an apparatus for the application of biological samples to an electrophoretic slab support, in particular an electrophoresis gel, characterized in that it comprises:

—one or more planar elements made of porous material on which a biological sample can be loaded, these planar elements being

* either resting on the edge of a planar porous membrane, joined to the porous membrane, extending in the same plane as the latter and acting as a projection of the said porous membrane—these elements being designated hereafter "projecting elements"—, the projecting part of these elements not joint to the porous membrane having a free end,

* or independent of each other, attached to common stiffening devices which maintain in the same plane, these elements projecting out from the stiffening devices—these elements being designated hereafter "projecting elements"—the stiffening devices being such that their form and their dimensions are compatible with those of the projecting elements so as to make possible the support of one part of each projecting element by the stiffening devices under conditions such that the stiffening devices do not hinder the placing in contact of the projecting elements with the plane surface of the electrophoretic slab support and the loading of the biological sample onto the electrophoretic slab support, each of the above-mentioned projecting elements comprising means for the partitioning and/or retention of the biological sample which prevent a biological sample loaded onto one of the above-mentioned projecting elements from spreading over the surface of the said projecting element, and/or seeping out over the surface of the said projecting element without preventing the loaded biological sample from diffusing right to the end of the said projecting element, which is desired to be placed in contact with the electrophoretic slab support, the above-mentioned projecting elements being such that they all have at least one point capable of being placed in contact with the planar surface of the electrophoretic slab support in order that one or more biological samples can be loaded onto the said support, each biological sample being loaded beforehand onto one element of the projecting elements, these different points being capable of being simultaneously placed in contact with the surface of the said slab support as a result of an alignment, when the above-mentioned porous membrane or the above-mentioned stiffening devices are arranged in an inclined or perpendicular plane with respect to the surface of the above-mentioned slab support.

The apparatus of the invention makes it possible to carry out the loading of biological samples, in particular onto an agarose or acrylamide gel or onto a membrane cellulose acetate.

The porous membrane and the projecting elements advantageously have a thickness of about 50$\mu$ to about 200$\mu$, and preferably of about 100 to about 150$\mu$.

The apparatus of the invention is such that it makes it possible to carry out the loading of a biological sample without liquid transfer but by diffusion (constituents contained in the biological sample) between two solid media which are respectively all of the projecting elements and the electrophoretic slab support, each being saturated with liquid in order to prevent transfer from one to the other. Under these conditions, very fine loading can be obtained, particularly if the zone of contact between the end of the projecting elements (i.e. the cross-section of the projecting elements) and the slab support are very small.

The apparatus for the application of biological samples is preferably designed for the application of the said samples onto an electrophoresis gel.

The biological sample is constituted by a solution containing components to be determined. As examples, mention may be made of serum, urine, etc. . .

According to an advantageous embodiment, the apparatus of the invention comprises:

—a planar porous membrane including on one of its edges at least one and preferably several projecting elements made of porous material, these projecting elements being joined to the porous membrane and lying in the same plane as the latter, the part of the projecting elements not joined to the porous membrane having a free end, the porous membrane and the projecting elements having a thickness of about $50\mu$ to about $200\mu$, and advantageously of about 100 to about $150\mu$, the projecting elements being such that they all have at least one point capable of being placed in contact with the planar surface of the electrophoretic slab support in order that one or more biological samples can be loaded onto the said slab support, each biological sample being loaded beforehand onto one element of the projecting elements, preferably onto the free end of this projecting element, the different points being capable of being simultaneously placed in contact with the surface of the said slab support as a result of an alignment, when the above-mentioned porous membrane is arranged in a plane which is inclined or perpendicular with respect to the surface of the above-mentioned slab support.

The apparatus of the invention thus comprises a porous membrane, the pores of which can absorb the sample and can, if necessary, also absorb a humidification liquid.

The biological sample preferably loaded close to the end of a projecting element, is absorbed by capillary action into the pores of the porous membrane up to a certain height (called "sample front") depending on the volume loaded, the size of the projecting element, its thickness and the degree of porosity of the material of which the projecting element is constituted.

According to an advantageous embodiment, the apparatus of the invention comprises means for the humidification of the projecting parts, whether separable or not from the above-mentioned porous membrane.

The humidification liquid is incorporated into the porous membrane, above the front of the biological sample. If the humidification liquid is introduced into the porous membrane at least to saturation and preferably in excess with respect to the absorption capacity of the porous membrane, it migrates by capillarity to the level attained by the sample and it maintains the sample there where the latter is absorbed.

It may be said that the porous material is saturated with liquid if the total volume of its pores is occupied by liquid. Thus, a porous membrane with a degree of porosity of 60% is at saturation when it contains liquid corresponding to 60% of its volume and a porous membrane with a degree of porosity of 90% is at saturation when the liquid it contains corresponds to 90% of its volume.

Furthermore, if an evaporation of the solution containing the sample occurs, the humidification liquid which saturates the porous membrane and which is advantageously introduced in excess with respect to the absorption capacity of the porous membrane will replace the solvent of the sample solution which has evaporated, and which will return the sample towards the end of the projecting elements and lead to its concentration.

The presence of the humidification liquid in the membrane made of porous material creates a flux directed from the porous membrane towards the ends of the projecting elements which results in the biological sample being returned towards the respective ends of the projecting elements.

The biological sample, loaded preferably at the end of a projecting element, diffuses from the end of the projecting element upwards for a distance of about 1 to about 10 mm, in particular from about 3 mm to about 5 mm, the limit of this upward movement constituting a line of equilibrium between the diffusion of the sample, on the one hand, and the reversal of flow created by the humidification liquid, on the other.

When the distance of the sample front from the end of the projecting element is reduced as a consequence of the reversal of flow of the sample by the humidification liquid, there is concentration of the sample. In an extreme case, the sample front may be situated after the concentration phase at a distance of 0.5 or 0.3 mm from the end of the projecting element which corresponds to a concentration of up to a factor of 20 or 30 in the case when the front was initially 10 mm high.

According to an advantageous embodiment of the invention, conditions are used such that the biological sample is concentrated at the end of the projecting elements since this makes it possible to use dilute biological samples without the intervention of a prior concentration step.

In fact, the concentration of the sample takes place in the apparatus of the invention.

For example, the diffusion of the biological samples and their concentration towards the end of the projecting elements is brought about by accelerating the flux created by the humidification liquid, this flux being directed from the porous membrane towards the end of the projecting elements on which the biological samples are loaded, by accelerated evaporation of the sample liquid by the use of a current of air either at room temperature or at a temperature preferably lower than or equal to about 40° C.

This concentration procedure may vary depending on the types of analysis envisaged. The concentration factor may vary from about 1.2 to about 3 in the case of the protein analysis of a serum, by a factor of about 2 to about 5 in the case of the lipid analysis of a serum, by a factor of about 10 to about 30 in the case of the analysis of proteins in a urine or in a cerebral-spinal fluid.

The volume of the biological sample loaded onto the electrophoresis gel varies from 0 to the total volume of the biological sample loaded onto the end of the projecting elements.

More specifically, with regard to the volume of the biological sample loaded onto a projecting element, it is such that the biological sample spreads from the end of the projecting element to a level called the sample front situated at a distance from the end of the projecting element of 1 mm to 10 mm, in particular from about 3 mm to about 10 mm. As indicated above, this distance also depends on the length of the projecting element, its thickness and the degree of porosity of the material of which the projecting element is constituted.

For degrees of porosity varying from about 50% to about 90%, the loading volume of a biological sample onto a projecting element varies from about $0.05 \cdot 10^{-2}$ to about $1 \cdot 10^{-2}$ μl/mm and per μ of thickness of the porous material, and preferably from about $0.15 \cdot 10^{-2}$ to about $0.5 \cdot 10^{-2}$ μl/mm and per μ of thickness of the porous material.

As far as the electrophoresis gel is concerned, this latter is always saturated with liquid in accordance with the preceding specification since even if it undergoes partial dehydration, the pores collapse, i.e. there is a diminution of the volume of the pores which are nonetheless still occupied by liquid.

In the case in which the porous material is saturated with liquid, the passage from the end of the projecting elements into the gel of the substances contained in a part of the volume (loaded onto the extremity of the projecting elements) of the biological sample thus occurs by diffusion and not by transfer of the solution (containing the substances to be determined) represented by the biological sample.

Once the porous material is not saturated with liquid, there will occur the transfer of liquid from the gel towards the porous material as a result of a capillarity phenomenon, which counteracts the diffusion of these molecular species into the gel. This phenomenon is greater the further removed the porous material is from saturation.

It can be estimated that once the amount of liquid impregnating the porous material is less than or equal to 90% of the quantity of liquid impregnating it at saturation, no further loading can be effected.

For sematic reasons, the expression "amount of biological samples loaded onto the slab support or onto the gel" designates in the foregoing and in what follows the amount of substances to be analysed contained in a part of the volume of the biological sample loaded onto the end of the projecting elements and which has diffused into the gel.

The amounts of the substances to be determined contained in a part of the volume of the biological sample deposited on the electrophoresis gel must be, on the one hand, such that the substances to be determined are present in the slab support or the gel in sufficient quantity for them to be detected and, on the other, such that the substances to be determined are not present in amounts greater than the amount above which resolution becomes inadequate.

As for the amount of the substances to be analysed, loaded onto the slab support or the gel it depends, on the one hand, on the time of flow reversal or concentration of the biological sample at the end of the projecting element and, on the other, on the time of application from the end of the projecting element on to the slab support or onto the gel.

It also depends on the substances to be analysed.

As an example, in the case of the determination of proteins contained in a serum, the amounts to be loaded onto the gel vary depending on the sensitivity of the stain used and hence the concentration time for the biological sample at the end of the projecting elements and the application time to the electrophoretic slab support vary as a function of the stains selected to reveal the proteins under investigation.

In the case of a relatively insensitive stain such as Ponceau red, the phase of concentration by means of evaporation in air of the solution of the biological sample should be for example 5 minutes (sample concentrated about 1.8 fold) before loading with an application time to the gel of one minute. Under these conditions, the amount of substances to be analysed loaded per mm is that contained in about 0.06 μl of the initial sample.

In the case of a more sensitive stain, for example Amido Black the phase of concentration by evaporation in air of the solution of the biological sample should be for example 2 minutes (sample concentrated about 1.3 fold) before loading with an application time to the gel of 30 seconds. Under these conditions, the amount of substance to be analysed loaded per mm is that contained in about 0.02 μl of the initial sample.

In the case of an even more sensitive stain, for example Acid violet, the phase of concentration by evaporation in air of the solution of the biological sample should be for example 2 minutes (sample concentrated about 1.3 fold) before loading with an application time to the gel of 15 seconds. Under these conditions, the amount of substance to be analysed loaded per mm is that contained in about 0.01 μl of the initial sample.

As an example in the case of a lipid analysis, the phase of concentration by evaporation in air of the solution of the biological sample should be for example 10 minutes (sample concentrated about 2.7 fold) before loading with an application time to the gel of about 2 minutes. Under these conditions, the amount of sample loaded per mm is that contained in about 0.12 μl of the initial sample.

As an example in the case of the determination of LDH (lactate dehydrogenase) isoenzymes, the phase of concentration by evaporation in air of the solution of the biological sample should be for example 6 minutes (sample concentrated about 2 fold) before loading with an application time to the gel of 2 minutes. Under these conditions, the amount of sample loaded per mm is that contained in about 0.1 μl of the initial sample.

As for the porosity, it is defined by two parameters which are the degree of porosity, i.e. the ratio between the total volume of the interstices occupied by the pores and the total volume of the material, and the size of the pores.

The degree of porosity of the material varies from about 50% to about 90%.

As for the size of the pores, it varies from about 0.2μ to about 20μ, and advantageously from about 2μ to about 10μ, and most advantageously is about 8μ.

If the pores are too small, the reversal of flow and possibly the concentration at the end of the projecting elements requires too long a time. If the pores are too large, the biological sample siphons through the pores (driven by the humidification liquid); in this latter case, transfer rather than diffusion takes place and there is loss of fineness of loading.

However, in order to prevent the siphonning phenomenon, it is possible to modify the viscosity of the humidification liquid, for example by using a polymer advantageously possessing the same properties as the polymers defined below with respect to the sharpness of the biological sample front.

As for the contact between the ends of the projecting elements and the slab support, it occurs when the angle between the slab support and the ends of the projecting elements is about 45° to about 90°, and advantageously about 90°.

As for the humidification of the porous membrane, the humidification liquid may be deposited each time the device is used with the aid of any means for doing so, such as a pipette.

As for the humidification it may take place either before (insofar as the front of the humidification liquid has not yet attained the zone where the loading of the sample must occur), or preferably after the loading of the sample onto the ends of the projecting elements.

When the projecting elements are placed in contact with the gel, it is not necessary that the reserve of liquid which has made the humidification and hence the reversal of flow of the biological sample (and possibly the concentration of the biological sample at the end of the projecting elements) possible is still present insofar as the loading of the sample onto the gel follows immediately after the humidification phase or insofar as the loading of the sample on to the gel follows immediately after the humidification—and possibly the concentration of the sample at the end of the projecting elements.

In the first stage for example it is possible to immerse the part opposite to the projecting elements in a humidification solution placed in a reservoir separate from the apparatus of the invention, then to immediately carry out the placing of the ends of the projecting elements thus treated in contact with the gel.

However, specific humidification agents may be bound to the membrane in a reversible or irreversible manner. These agents may be composed of a material capable of receiving the humidification liquid or consist of a reservoir capable of containing the humidification liquid.

According to an advantageous embodiment of the invention, the humidification agents are situated above the area surrounding the front of each biological sample loaded onto each projecting element and advantageously above the parts of the porous membrane joint to the projecting elements.

The distance between the humidification agents and the front of each sample varies from about 1 mm to about 20 mm, and is advantageously about 2 mm.

As material capable of receiving the humidification liquid, it is possible to use a material capable of being impregnated, such as a spongy material, for example a natural or synthetic sponge, or filter paper of adequate thickness, advantageously between about 0.5 mm and about 3 mm of agarose gel.

The spongy material capable of being impregnated with a humidification liquid is such that it may contain a quantity of liquid varying from about 2 fold to about 20 fold the weight of the said material. This material impregnated with humidification liquid may also be a gel, for example agarose gel.

According to an advantageous embodiment of the invention, each projecting element is in contact with the gel over a length varying from 1 mm to about 200 mm, and preferably from about 1 mm to about 40 mm, depending on which biological sample is loaded onto the gel.

According to another embodiment of the invention, the porous membrane has a quadrilateral form, in particular square or trapezoidal, and advantageously rectangular, one of the sides of which is joined to the projecting elements. The free end of the above-mentioned projection elements is in particular constituted by polygons such as triangles, trapezes, rectangles, squares, parts of a disc or parts of an ellipse.

The projecting elements are advantageously constituted by strips in the form of squares or rectangles, separated one from the other.

Advantageously, these strips have a length of contact with the gel of about 1 to about 200 mm, in particular of about 1 to about 40 mm, and are separated from each other by a distance of at least about 0.5 mm.

The projecting elements are advantageously obtained by cutting them out from the porous membrane along one of its edges.

According to an advantageous embodiment of the invention, the porous membrane and the projecting elements are constituted by the same porous material.

The material of the porous membrane and the projecting elements are advantageously composed of hydrophilic material, such as cellulose or a cellulose derivative, such as the cellulose esters (cellulose acetate, cellulose propionate, cellulose nitrate . . . ) or mixed esters of cellulose. It may also be composed of nylon, or of a hydrophobic material such as polyethylene, polypropylene or polycarbonate.

Other porous materials which may be considered are regenerated cellulose, polyvinylidene fluoride, polysulfone or modified polysulfone.

When it is desired to reduce the absorption time of the samples or of the humidification liquid in the pores of the porous membrane, either when the latter is insufficiently hydrophilic (as for example certain cellulose nitrates), or when it possesses a very small pore size (for example less than about $0.5\mu$) it is preferable, before using the porous membrane to have recourse to the incorporation of a wetting agent of a type and in an amount such that it does not denature the components contained in the sample to be analysed. This wetting agent is used in sufficient quantity in order that the sample loaded on each projecting element can penetrate by absorption into the porous material within a relatively short time of less than about 10 seconds. The wetting agent advantageously consists of glycerol, 1,3-butanediol or uncharged surfactants such as Triton X100® and Tween®, used advantageously at concentrations between about 0.001% and about 10%.

As for the absorption of the humidification liquid by the porous material, the use of a wetting agent is particularly advantageous when the humidification agents consist of a material capable of receiving the humidification liquid and capable of transferring the humidification liquid perpendicularly to the porous membrane. This is the case when the humidification agents are applied in a reversible or irreversible manner to the porous membrane, this application leading to the existence of zones which are not humidified, a circumstance which creates perturbations in the process of the reversal of flow of the biological sample towards the ends of the projecting elements.

However, when the humidification agents consist of a reservoir, situated above the edge of the porous membrane, opposite to the projecting elements, it is possible not to use a wetting agent (in this case, the liquid is transferred in a parallel manner to the surface of the porous membrane).

According to another advantageous embodiment of the invention, the apparatus comprises:
—stiffening devices for the porous membrane,
—and/or agents for binding the porous membrane to a system of application of the biological samples which can be automated.

The stiffening devices for the porous membrane may be composed of a stiffening support for the porous membrane, the form and the dimensions of which are compatible with those of the porous membrane and those of the projecting elements, so as to make possible the maintenance of one part of the porous membrane by the stiffening support under conditions such that the support does not hinder either the placing in contact of the projecting elements joined to the porous membrane with the planar surface of the electrophoresis gel or the loading of the biological sample onto the electrophoresis gel.

The stiffening support may be composed of two elements between which a part of the membrane is inserted.

The binding agents may be constituted by a clamp or any technical equivalent capable of holding the porous membrane, if necessary stiffened by a support.

The binding agents may also be such that they confer on the membrane a suitable rigidity and be such that they are capable of comprising agents making it possible to constitute a reservoir capable of humidifying the porous membrane.

As an example, the porous membrane may be inserted between two parts of magnetic material, at least one of which is flexible in order to ensure impermeability, each of the parts of the magnetic material being itself in contact with a rigid supporting element.

According to another embodiment of the invention, the apparatus of the invention comprises:

—stiffening devices, in particular a stiffening support for the porous membrane, the form and the dimensions of the stiffening devices being compatible with those of the porous membrane and of the projecting elements so as to ensure the support of at least a part of the porous membrane by the stiffening devices under conditions such that the stiffening devices do not hinder the placing in contact of the projecting elements joined to the porous membrane with the planar surface of the electrophoretic slab support and the loading of the biological sample onto the electrophoretic slab support, —this apparatus being such that, if necessary, either the porous membrane, or the stiffening devices, or both of them include humidification agents for the projecting parts, these humidification agents being advantageously constituted in the case of the porous membrane, by a material capable of being impregnated with a humdification liquid such as a spongy material bound reversibly or irreversibly to the said membrane, in the case of the stiffening devices, by a reservoir integrated into the said stiffening devices or detachable from the said devices, or resulting from a space formed by the configuration of a part of the stiffening devices and by a part of the porous membrane, in the vicinity of the edge of the porous membrane opposite to that which bears the projecting elements, the said reservoir containing a humidification solution, and waterproofing agents between itself and the porous membrane or by a material capable of being impregnated with a humidification liquid, such as a spongy material, detachable or not from the stiffening devices, the humidification solution being water or an aqueous solution containing advantageously glycerol at concentrations of 0 to about 50% by volume, or a salt solution such as a solution of 0.15M phosphate buffer, 0.15M trisglycine buffer, 0.15M citrate buffer or a solution containing NaCl, advantageously 0.15M, etc. . .

When the apparatus of the invention comprises a stiffening support, the reservoir may be formed by the porous membrane and a part of the stiffening support, the said part of the support having a form and a lay-out with respect to the membrane such that there is a space in the vicinity of the upper part of the membrane in contact with the membrane, the said space being capable of receiving a humidification liquid.

According to an advantageous embodiment, the humidification solution advantageously contains a polymer making is possible to reduce the diffusion phenomena when the sample is returned towards the part of the porous membrane opposite the projecting elements.

As to the utilization of the apparatus of the invention, when the biological sample is loaded onto the end of the projecting parts, certain zones are impregnated before others by the biological sample, which may create an irregular front of the biological sample loaded onto the said projecting parts. In order to prevent these irregularities from becoming more pronounced during the concentration phase by the humidification solution, recourse is had to a polymer which, on account of its viscosity, has the function of ensuring the sharpness of the sample front, i.e. of making and maintaining the front of the biological sample approximately straight. In the case in which the projecting elements have the form of a rectangle, the role of the polymer is to make the front approximately parallel to the edge of the end of the said projecting elements.

Advantageously, the polymer used is a water-soluble polymer, of high molecular mass between about $2 \times 10^5$ and about $10^7$, such as hydroxyethylcellulose, dextran, polyacrylamide etc. . . at concentrations sufficient to ensure that the front of the sample loaded onto the projecting elements is approximately straight and at concentrations lower than that at which the humidification solution no longer diffuses owing to the breaking effect caused by the viscosity. The above-mentioned polymer advantageously has a concentration between about 0.05% and about 10%.

According to another embodiment of the invention, the porous membrane is a cellulose acetate sheet, advantageously rectangular or square, in which the projecting elements are constituted by strips separated from each other, situated on one side of the membrane, and the stiffening support includes a reservoir integrated into the support.

According to another embodiment of the invention, the device of the invention comprises:
—a porous membrane constituted by a sheet of paper, advantageously square or rectangular, in which the projecting elements are constituted by strips situated on one side of the porous membrane and separated from each other,
—a stiffening support,
—a spongy material capable of being bound in a detachable manner to the porous membrane or to the stiffening support.

According to another embodiment of the invention, the device of the invention comprises:
—a porous membrane constituted by a sheet of paper, advantageously square or rectangular, in which the projecting elements are constituted by strips separated from each other, situated on one side of the membrane,
—a stiffening support,
—a spongy material, bound in a detachable or undetachable manner to the above-mentioned porous membrane.

According to another embodiment of the invention, the porous membrane and the electrophoretic support include a pair of electrodes so as
—on the one hand, to create an electric field, after the loading of the biological sample onto the gel, between the porous membrane and the electrophoretic slab support, this field being capable of causing the biological samples to migrate from the projecting elements onto the slab support and thus load them onto the slab support,
—on the other hand, to apply a voltage to the electrophoretic slab support in order to cause the various constituents of each biological sample loaded onto the gel to migrate in a differential manner,
—this pair of electrodes being constituted by an electrode connected to the negative pole of a generator and, for example, situated at the edge of the porous membrane opposite to that which is joined to the projection elements and a positive electrode connected to the positive pole of a generator, situated at the end of the electrophoretic slab support opposite to that in the vicinity of which the biological samples are loaded.

In this embodiment of the invention, the fastest moving molecules migrate first and, in order to obtain a representative analysis, it is necessary to transfer to the gel the whole of the biological sample loaded on the projecting elements.

The use of such a device may be advantageous when working with dilute samples.

In this case, when all of the substances contained in the sample have migrated from the porous material onto the gel, the electrophoresis has already started, the application is interrupted and the negative pole of the generator is connected to the end of the electrophoretic support in the vicinity of which the biological samples were loaded and the electrophoresis is then continued in the usual way.

The invention also relates to a device in which the loading volume of a biological sample onto a projecting element is about $0.05\times10^2$ to about $1\times10^{-2}$ μl/mm, per μ of thickness of the porous material, and preferably between about 0.15 and about $0.5\times10^{-2}$ μl/mm, for a porosity of the porous material of between about 50% and about 90%, and the loading volume of the biological sample on the electrophoretic slab support is sufficient for the components in a sample to be detected and less than the value beyond which the resolution is inadequate.

In the case of independent projecting elements, the amounts of sample loaded are in excess with respect to the absorption capacity of the porous membrane. For example, in the case of a porous membrane element with a degree of porosity of 80%, and a surface area of 100 mm$^2$ and a thickness of 100μ, the amount of sample loaded will be greater than $0.8\times100\times0.1$, i.e. greater than 8 μl.

In practice, an excess of 1.5 to 3 times the absorption capacity of the porous membrane element should be loaded. Beyond that there is a risk that the hydrophobic barrier can no longer play its role with running off of the sample drop loaded in excess to the end of the projecting element.

The invention also relates to an apparatus for the application of biological samples to an electrophoretic slab support, characterized in that it comprises:

—one or more planar elements made of porous material, independent of each other and attached to common stiffening devices, in particular a stiffening support which hold them in the same plane, these elements projecting with respect to the stiffening agents—these elements being designated hereafter as projecting elements"—, these projecting elements possessing:

—two surfaces, one of which is at least in part supported by the stiffening devices and the other surface is the reverse of the one previously defined, —two longitudinal sections, —two ends corresponding approximately to transverse sections, one of these sections being designed to be applied to the electrophoretic slab support and being designated as "lower transversal section" (close to the lower end) and a transverse section opposite to that previously defined and designated as "upper transverse section" (in the vicinity of the upper end), —the stiffening devices being such that their form and their dimensions are compatible with those of the projecting elements, so as to make possible the support of a part of the projecting elements by the stiffening devices under conditions such that the stiffening devices do not hinder the placing in contact of the projecting elements with the planar surface of the electrophoretic slab support and the loading of the biological sample on the electrophoretic slab support, each of the above-mentioned projecting elements including means for partitioning and/or retention which prevent a biological sample loaded onto one of the above-mentioned projecting elements from spreading on the surface of the said projecting element, and/or seeping out over the surface of the said projecting element without preventing the loaded biological sample from diffusing to the lower transverse section of the said projecting element, designed to be placed in contact with the electrophoretic slab support, the projecting elements having advantageously a thickness of about 50μ to about 200μ, and preferably of about 100 to about 150μ, the above-mentioned projecting elements being such that they all have at least one point capable of being placed in contact with the planar surface of the electrophoretic slab support so that one or more biological samples can be loaded onto the said slab support, each biological sample being loaded beforehand onto one element of the projecting elements, preferably in proximity to the upper transverse section of the projecting element, these different points being capable of being placed simultaneously in contact with the surface of the said slab support as a result of an alignment, when the above-mentioned stiffening devices are arranged in a plane inclined or perpendicular with respect to the surface of the above-mentioned slab support.

In this configuration, the biological sample diffuses to the interior of the porous membrane and, preferably, none of the biological samples exudes at the surface of a projecting element.

According to another embodiment of the invention, the apparatus comprises:

—a set of projecting elements constituted by polygons such as triangles, trapezes, rectangles, squares, parts of discs or parts of ellipses, these projecting elements being advantageously constituted by strips in the form of squares or rectangles separated from each other, these strips having a length of contact with the gel of about 1 to about 200 mm, and in particular from about 1 to about 40 mm, and being separated from each other by a distance of at least about 0.5 mm.

The invention also relates to a device in which the projecting elements are constituted of a hydrophilic material, such as cellulose or a cellulose derivative, a cellulose ester, such as cellulose acetate, cellulose propionate, cellulose nitrate or mixed esters of cellulose or even nylon or a hydrophobic material such as polyethylene, polypropylene or polycarbonate.

The invention relates to an apparatus in which each projecting element is fitted with means which prevent a biological sample, loaded in the proximity of the upper transverse section of the said projecting element, from spreading over its surface, these means being advantageously constituted by a surface made of a hydrophobic material, such as a strip preferably attached to at least a part of the surface of the projecting elements which is opposite to the surface, a part at least of which is maintained by the stiffening support, the surface area of this hydrophobic material varying advantageously from about one fifth to approximately the whole of one of the two surfaces of the projecting element.

In the case of a strip, there is retention of the biological sample.

More precisely, the projecting elements are cut in the form of squares or rectangles and are attached to a rigid support, for example by glueing. A strip (for example a hydrophobic self-adhesive paper) is placed on the central part of the projecting elements. It plays the role of a barrier between the lower part and the upper part of each element of the porous membrane.

The sample is deposited in excess on the porous membrane, for example by means of a pipette in proximity to the upper transverse section or on the upper transverse section of the projecting element, above the strip. This strip placed on the surface of the porous membrane will prevent the sample from spreading over the surface of the projecting element, but will not prevent it from diffusing, by means of capillarity to the interior of the projecting element and reaching the lower end.

The sample having been loaded in excess with respect to the saturation of the porous membrane, the sample drop remaining above the strip will play the role of reserve of humidification liquid.

The above-mentioned apparatus is effective when the porous membrane has a relatively small size, i.e. less than about 3μ.

In the case of a porous membrane having a large pore size (larger than about 3μ, even larger than about 5μ), the apparatus mentioned above can not function.

In fact, when the size of the pores is large and if the humidification liquid is not sufficiently viscous, the liquid siphons through the pores and a transfer of liquid is produced when the samples are applied to the gel resulting in non-focussed loads.

In the case of a pore size greater than about 3μ, the invention offers an apparatus in which each projecting element is fitted with means which prevent a biological sample, loaded at the proximity of the upper transverse section of the said projecting element, from spreading over its surface and seeping out over its surface, these means being advantageously constituted by a hydrophobic material, coating the two surfaces of the projecting element (as well as the longitudinal sections, if necessary), to the exclusion of the two transverse sections, advantageously to the extent of from about 20% to about 100% of the two surfaces upwards from their lower transverse section, in particular to the extent of 100% of the surface maintained by the stiffening support and about 20% to 100% of the surface opposite to this surface, and coating in particular the whole of the two above-mentioned surfaces with the exclusion of the two transverse sections.

In the case in which one of the surfaces is only coated partially by the hydrophobic material, in particular the surface opposed to that maintained by the stiffening support, it is necessary that the zone in proximity to the lower transverse section be coated with a hydrophobic material in order to prevent seeping out. That is the reason why it is essential to specify that the coating of the two surfaces, when it is partial, occurs upwards from the lower transverse section.

Each projecting element (of high porosity) is film coated on its two surfaces with a hydrophobic coating, except for the two transverse sections.

In the case of a hydrophobic coating, there is retention and partitioning of the biological sample.

The projecting elements are attached, at least in part, for example by glueing, to stiffening agents, such as a stiffening support.

In other words, the projecting elements are, in the proximity of the lower transverse section, coated with a hydrophobic film and are hence impermeable to the water which can cover the whole of the projecting element, with the exception of the two transverse sections, and possibly with the exception of a part of the surface opposite to that maintained by the stiffening support provided that this uncoated zone is not joined to the lower transverse section, in order to avoid the seeping out of the biological sample.

The sample is loaded in excess, for example by means of a pipette, on the uncoated zone, advantageously on the upper transverse section. The sample diffuses by capillarity into the projecting element at the interior of the hydrophobic coating until it reaches the end of the projecting element which, not being film-coated on its lower transverse section, will make possible the loading of the sample when it is applied to the gel.

The fact of having coated the surface of each projecting element with a hydrophobic film (from several microns to several tens of microns thick, and advantageously about 5μ to about 30μ thick) prevents the liquid from seeping out transversally by siphonning from the interior of the projecting element towards its surface, which would lead to an accumulation of sample liquid at its surface which would then run along this surface until it reaches the end of the projecting element to give a large unfocussed load.

By making each projecting element impermeable, the only movement of the sample liquid is a longitudinal movement, which occurs very slowly, given the large distance to be covered and the considerable loss of load at the pores, whereas the transverse movement of liquid exudation which occurs in the absence of waterproofing takes place much more readily (short distance to be covered since the porous membrane is very thin: 50 to 200μ).

Furthermore, in the absence of waterproofing, the resultant of the exudation phenomenon is amplified at the end of each projecting element, since all of the liquid which has seeped out transversally accumulates there by gravity.

This hydrophobic coating may be produced by spraying or coating or film formation on each projecting element of hydrophobic substances such as silicone, paraffin, polytetrafluoroethylene, latex, a plastic such as polyethylene, or any coating making it possible to waterproof the surface of the porous membrane without penetrating into it while adhering to it.

In the case in which the apparatus of the invention comprises independent projecting elements, the loading volume of a biological sample onto a projecting element is about $6 \times 10^{-4}$ to $27 \times 10^{-4}$ μl/mm² per μ of thickness of the porous material, for a degree of porosity of about 50% to about 90%.

The invention also relates to an apparatus in which each projecting element possesses a length of contact with the gel of about 1 mm to about 200 mm, and preferably from about 1 mm to about 40 mm, depending on which biological sample is loaded onto the gel.

The invention also relates to an apparatus according to which the porous membrane and/or the projecting elements are constituted of a hydrophobic material containing a wetting agent of the type and in an amount such that it does not denature the components contained in the sample to be analysed, this wetting agent being in an amount such that the sample can be loaded in sufficient quantity on one of the projecting elements and in an amount lower than that at which the biological sample can no longer be concentrated at the extremity of the projecting element, the wetting agent being constituted advantageously by glycerol, 1,3-butanediol or uncharged surfactants such as Triton X-100®, Tween® advantageously used at concentrations from about 0.001% to about 10%.

The invention relates to a procedure for loading one or more biological samples onto an electrophoretic slab support, in particular an electrophoresis gel, characterized in that —biological samples are loaded onto one and advantageously several projecting elements made of porous material and joined to one of the edges of a planar porous membrane and as an extension in the same plane of the latter, the loading of the biological samples being performed, in particular at the free end of the said projecting elements, these projecting elements being such that they all have at least one point capable of being placed in contact with the planar surface of the said electrophoretic slab support, these different points being capable of being simultaneously placed in contact with the surface of the said slab support as a result of an alignment, when the above-mentioned porous membrane is arranged in an inclined or perpendicular plane with respect to the surface of the above-mentioned slab support,
—if necessary, at least a part of the above-mentioned porous membrane is attached to the stiffening devices, in particular a stiffening support,
—it is preferable to avoid the diffusion of the biological samples from the end of the projecting elements towards the porous membrane with the aid of agents for the humidification of the projecting elements, these humidification agents comprising a humidification liquid which, as a consequence of the evaporation of liquid from the biological sample, creates a flux from the porous membrane towards the end of the projecting elements and forces the biological samples towards the free end of the projecting elements, and which concentrates the biological sample at this end, these humidification agents comprising for example a spongy material attached in a removable or irremovable manner to the membrane or to the stiffening devices or a reservoir attached in a removable or irremovable manner to the above-mentioned stiffening devices,
—the projecting elements of the porous membrane, a part of which is possibly attached to a stiffening support are placed in contact with the electrophoretic slab support in order to cause diffusion of the sample from the projecting elements on to the electrophoretic slab support and to thus load it onto the said slab support.

The humidification, when it is done, must be sufficient so that the whole of the surface of the porous membrane, on the one hand, and the surface of the projecting elements free of the biological sample, on the other, are saturated with humidification liquid.

According to an advantageous embodiment of the invention, the diffusion of the samples from the ends of the projecting elements towards the porous membrane is prevented before or after the attachment of a part of the projecting elements of the porous membrane to a stiffening support.

When the humidification is done before the loading of the biological sample, it is necessary that the part of the ends of the projecting elements designed to receive the biological samples is not saturated with humidification liquid in order for it to be possible to load the biological sample.

According to another embodiment of the procedure of the invention, the diffusion of the biological samples and their concentration towards the end of the projecting elements is caused by creating a flux of the humidification liquid towards the end of the projecting elements on which the biological samples are loaded, for example by evaporation of the liquid of the biological sample or by accelerating this evaporation and the flux, for example by ventilation in a current of air at a temperature less than or equal to 40° C.

According to another embodiment of the invention, the loading of the biological samples onto the electrophoretic slab support is done while an electric current is applied to the porous membrane and the projecting elements, the humidification liquid being constituted by a buffer solution at a pH such that all of the molecular species of the sample to be analysed are ionized and acquire a charge of the same sign, this charge being negative if the pH is one unit higher than the isoelectric point of the most basic molecular species, or positive if the pH is one unit lower than the isoelectric point of the most acidic molecular species, by the intermediary:
—of an electrode connected to the pole of a generator situated for example at the edge of the porous membrane opposite to that which is joined to the projecting elements,
—of an electrode connected to the other pole of a generator situated at an extremity of the electrophoretic slab support, in the case in which all of the molecular species of the biological sample have a negative charge, the electrophoretic slab support will be connected to the positive pole and to the negative pole in the inverse case.

Generally speaking, in the case where it is desired to determine proteins in a serum, advantageously a pH of about 10 to 10.5 will be selected, i.e. a pH value higher than the highest isoelectric point.

In order to confer a negative charge on the molecular species, it is possible to use a Tris-HCl, glycinate or carbonate-bicarbonate buffer, etc. . .

In order to confer a positive charge on the molecular species, it is possible to use an acetic acid-acetate, citric acid-citrate buffer, etc. . .

The invention also relates to a procedure for the loading of one or more biological samples onto an electrophoretic slab support, characterized in that
—biological samples are loaded onto one or advantageously several planar elements, made of porous material, independent of each other and attached to common stiffening devices, in particular a stiffening support, which maintains the above-mentioned elements in the same plane, these elements projecting beyond the stiffening devices, these elements being designated hereafter as "projecting elements", these projecting elements possessing:
—two surfaces, one of which is at least in part supported by the stiffening devices and the other surface is the reverse of the one previously defined,
—two longitudinal sections,
—two ends corresponding approximately to transverse sections,
one of these sections being designed to be applied to the electrophoretic slab support and being designated as "lower transversal section" (close to the lower end) and a transverse section opposite to that previously defined and designated as "upper transverse section" (in the vicinity of the upper end),
—the stiffening devices being such that their form and their dimensions are compatible with those of the projecting elements, so as to make possible the support of a part of the projecting elements by the stiffening devices under conditions such that the stiffening devices do not hinder the placing in contact of the projecting elements with the planar surface of the electrophoretic slab support and the loading of the biological sample on the electrophoretic slab support, each of the said elements comprising means which prevent a biological sample loaded onto one of the projecting elements to spread over the surface of the said projecting elements, and/or to seep over the surface of the said projecting element, these projecting elements being such that they all have at least one point capable of being placed in contact with the surface of the chromatographic support, these different points being capable of being placed simultaneously in contact with the surface of the said support as a result of an alignment when the above-mentioned stiffening devices are arranged in an inclined or perpendicular plane with respect to the surface of the said slab support,
—the projecting elements attached to the stiffening support are placed in contact with the electrophoretic slab support so that the sample can diffuse from the projecting elements on to the electrophoretic slab support and thus be loaded onto the said slab support.

The invention also relates to a procedure using an apparatus of the invention in which one of the two above-mentioned surfaces of each projecting element is fitted with a strip placed in the vicinity of the central part of the projecting element and advantageously attached to at least a part of that surface of the projecting elements which is the reverse of the surface of which a part at least is supported by the stiffening support, thus dividing the projecting element into an upper part and a lower part, the size of the strip varying advantageously from about one fifth to practically the whole of one of the two surfaces of the projecting element.

—a biological sample is loaded in excess onto the abovementioned upper part of the projecting element, in particular in the vicinity of the upper transverse section, the biological sample thus loaded does not spread over the surface of the projecting element, diffuses to the interior of the projecting element and reaches the lower transverse section of the said projecting element in order to be loaded onto the electrophoretic slab support.

In this case, the biological sample may be concentrated by evaporation in air of a part of the liquid of the biological sample.

The invention also relates to a procedure using an apparatus of the invention in which each projecting element is coated with a hydrophobic material on both of its surfaces, and possibly on the two longitudinal sections, to the exclusion of the two transverse sections, this hydrophobic material being such that it coats about 20% to about 100% of the two surfaces upwards from their lower transverse section, in particular to an extent of 100% of the surface supported by the stiffening support and from about 20% to about 100% of the reverse surface, possibly including the two longitudinal sections, and that it coats in particular the whole of the two surfaces with the exception of the two transverse sections,
—a biological sample is loaded in excess onto an area of the projecting element not coated with a hydrophobic material, advantageously in the vicinity of the upper transverse section, and since the sample diffuses longitudinally into the interior of the hydrophobic film until it reaches the lower transverse section of the projecting element which is not coated, the loading of the biological sample onto the electrophoretic slab support is achieved by means of capillarity.

In this particular arrangement, it is not possible to concentrate the sample by evaporation of the sample liquid as was possible in the case of a porous membrane joint to projecting elements as indicated previously, in view of the fact that the sample situated close to the end of each projecting element is protected from evaporation (only the transverse section of the end is exposed to the air). In order to load variable amounts of sample, the only parameter which can be varied is the time of application to the gel.

The invention also relates to a loading procedure not followed by electrophoretic migration, such as the "crossdot" procedure or an immunofixation procedure.

In the case of a cross-dot, the procedure is as follows:
—the loading of a biological sample onto a slab support with the aid of projecting elements is performed in conformity with what has already been described, this loading not being followed by electrophoresis,
—then, in an approximately perpendicular direction, the loading of a reactive at right angles to the above load is carried out,
—incubation is allowed to proceed,
—the result of the reaction possibly formed between the biological sample and the reagent is revealed.

In the case of immunofixation, the procedure is as follows:
—a biological sample is loaded as indicated above,
—the electrophoretic migration is allowed to occur,
—and when the migration is complete, a reagent is loaded in a direction approximately perpendicular to the first load over a distance encompassing the entire electrophoretic migration,
—incubation is allowed to proceed,
—then the result of the reaction possibly formed between the biological sample and the reagent is revealed.

The space formed by the opening outwards of each of the supporting elements from the membrane constitutes a reservoir (D).

The cross-section view shows the cross-section of the apparatus along an axis perpendicular to the edge of the membrane containing the projecting elements and situated approximately in the middle of a projecting element of the membrane.

FIG. 2 presents a plan view and a cross-section view of an apparatus of the invention comprising a rectangular, porous, planar membrane (A) in which one of the edges contains rectangular projecting elements, this planar membrane being stiffened by a support (B), for example glued (in order to ensure impermeability between the stiffening support and the porous membrane) to the area to which the porous membrane is fitted, and which possesses a part which is opened out from the membrane; the space formed between the membrane and this convex part serves as a possible reservoir (D).

Figure 3A:
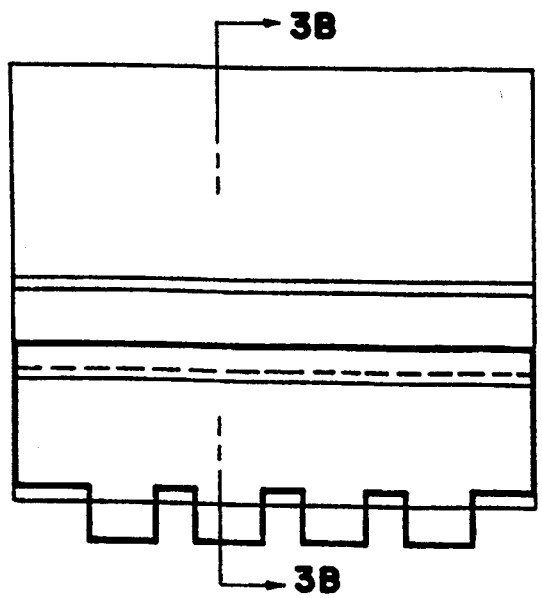
Figure 3B:
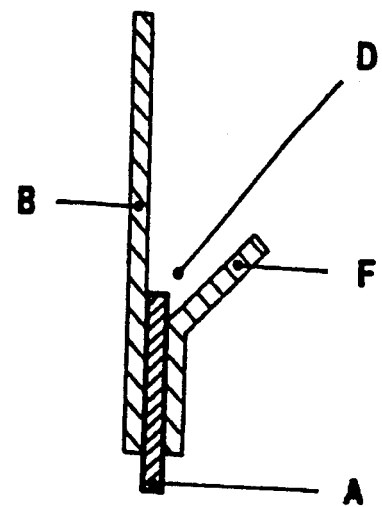

FIG. 3 presents a plan view and a cross-section view of an apparatus of the invention comprising a rectangular, porous, planar membrane (A) in which one of the edges contains rectangular projecting elements. This membrane is fitted onto a support (B), for example glued (in order to ensure impermeability between the stiffening support and the porous membrane) to the zone to which the porous membrane is fitted. A sheet (F) of flexible and hydrophobic material, for example paper, is applied to the surface of the membrane not fitted to the support. In the vicinity of the upper edge of the membrane this sheet opens outwards and the space formed between the support and the part of the sheet of material which opens outwards forms the reservoir (D).

FIG. 4 shows a plan view and a cross-section view of an apparatus of the invention comprising a membrane (A) having approximately the form of that described in FIG. 1 fitted against a flexible magnetized material (J) which has approximately the dimensions of the membrane, this flexible magnetized material (J) is itself fitted against one of the two elements (B) of a rigid support.

The element (B) of the support is articulated to the extent that with the other element (C) of the support it is capable of forming a clamp. The element (B) of the support has a rectangular form. The element (C) of the support has the form of a strip, which is articulated approximately in the middle of the upper part of the element (B) of the support. To the element (C) of the support is attached a flexible magnetized material (H) which has approximately the same dimensions as the membrane.

The plan view and the cross-section view present the clamp in the open position.

In the cross-section view, the circular arrow indicates the form to be adopted by the clamp in the-closed position. When the clamp is closed, the membrane (A) is then inserted and maintained between the two materials (H) and (J), which are fitted to the elements (C) and (B) of the support, respectively.

Figure 5A:
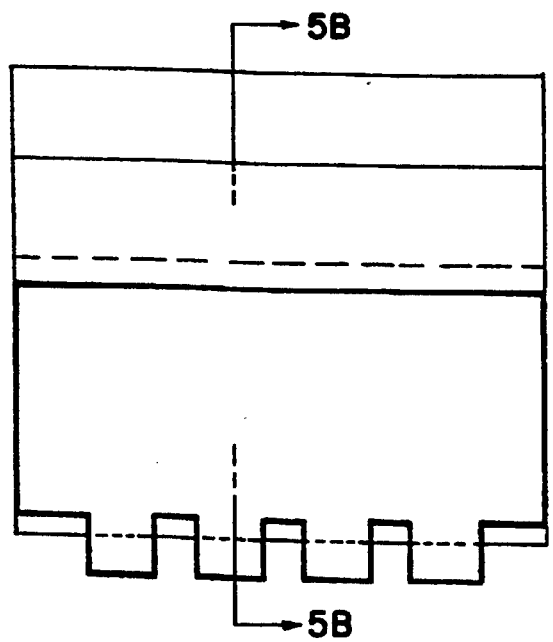
Figure 5B:
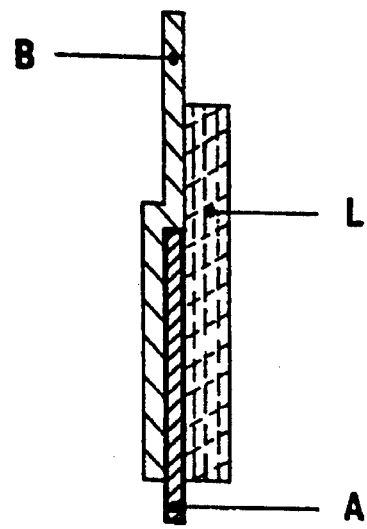

FIG. 5 presents a plan view and a cross-section view of an apparatus of the invention comprising a porous planar membrane (A) attached to a support (B). A spongy material (L), for example a sponge, filter paper or gel (for example agarose or acrylamide gel) is attached to the surface of the membrane not fitted to the support.

FIG. 6 shows a plan view and a cross-section view of an apparatus of the invention comprising a set of projecting elements (A) made of a porous material, maintained in the same plane by the intermediary of a stiffening support (B). A strip (N) made of hydrophobic material is applied in the median part of each of the elements.

Figure 7A:
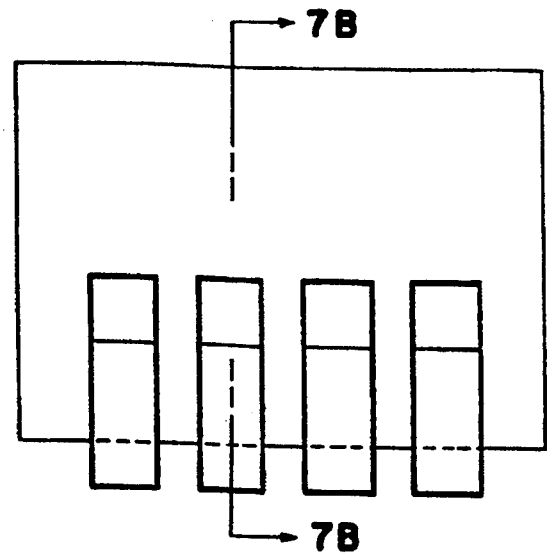

FIG. 7 shows a plan view and a cross-section view of a apparatus or,he invention comprising a set of projecting elements (A) made of a porous material and maintained in the same plane by the intermediary of a stiffening support (B). Each of the projecting elements is coated with a hydrophobic coating (P) both on the surface fitted to the support as well as on the opposite surface, with the exception of the two transverse sections.

As an example, FIG. 7 shows that the hydrophobic material does not cover the whole of that surface of the element not fitted to the support.

FIG. 8 presents a plan view and a cross-section view of an apparatus of the invention comprising a set of projecting elements (A) made of porous material, maintained in the same plane by the intermediary of a stiffening support (B) and does so, for example, by being glued to the lower part of their surface. The part of the projecting elements made of a porous material which is not glued is bent, for example, at 45° and the space created between the projecting elements (A) and the rigid support (B) forms the reservoir D in which the sample is loaded.

Figure 9A:
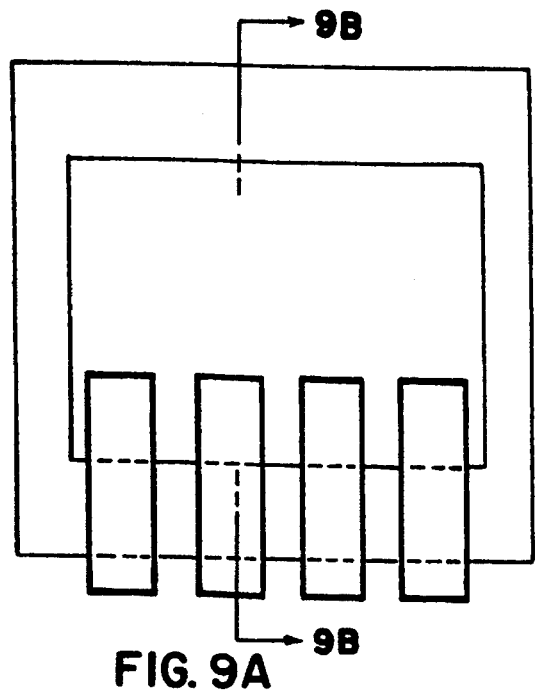
Figure 9B:
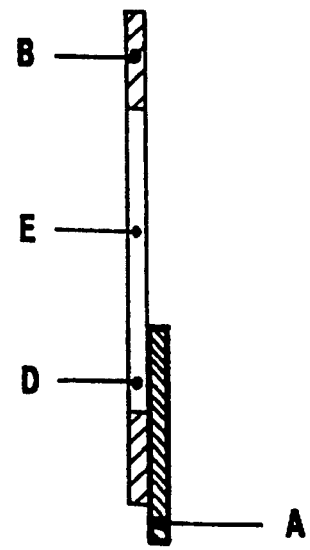

FIG. 9 shows a plan view and a cross-section view of an apparatus of the invention comprising a set of projecting elements (A) maintained in the same plane, for example, by glueing by means of the intermediary of a stiffening support (B). In this case, the stiffening support (B) possesses an opening E, which may be rectangular for example, such that the upper part of the elements (A) is located in this opening. The reservoir (D) in which the sample is loaded is then constituted by the lower horizontal part of the opening (E) in the support (B) and by the part of the element A which is not glued.

Figure 10A:
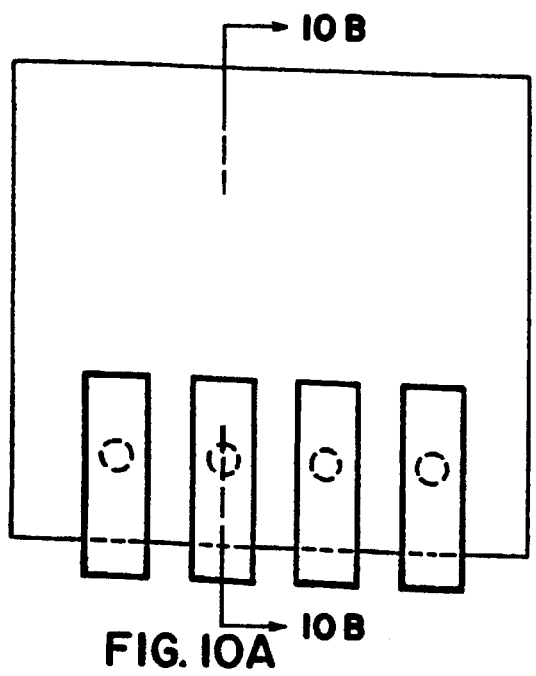
Figure 10B:
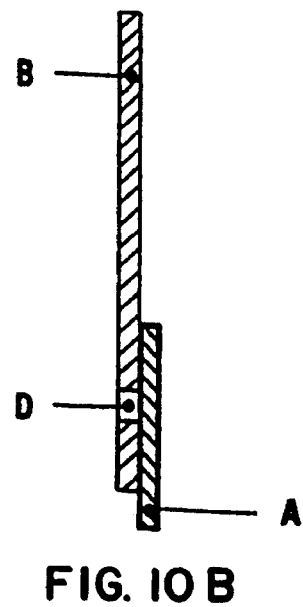

FIG. 10 represents a plan view and a cross-section view of an apparatus of the invention comprising a set of projecting elements A maintained in the same plane by the intermediary of a stiffening support (B) and which does so for example by glueing. The support (B) contains an opening (D) situated behind each of the elements (A). The reservoir (D) in which the sample is loaded is constituted in this case by this opening and that portion of the element (A) facing this opening.

The invention is illustrated by the examples below which are in no way limiting and which make reference to the figures which, for reasons of simplification, show four projecting elements, it being understood that the apparatuses used in the examples, when they make reference to a particular figure, may in actual fact possess a number of projecting elements different from four (for example one, six or eight).

EXAMPLE 1

PROTEIN ANALYSIS OF A SERUM INVOLVING STAINING WITH PONCEAU RED

A porous membrane of cellulose acetate having pore dimensions of 8μ and a thickness of 140μ is used, which comprises six projecting elements 4.0 mm in diameter and separated from each other by 2 mm. This membrane is attached to a rigid support (in conformity with the diagram shown in FIG. 1).

1 μl of pure serum is loaded by means of a micropipette onto each projecting element close to its end.

The reservoir (D) constituted by parts preglued to the porous membrane A is then loaded by means of a pipette with 400 μl of humidification liquid consisting of a 0.5% aqueous solution of polyacrylamide of molecular mass $5 \times 10^6$.

After exposure to air for 5 minutes, the apparatus is applied for one minute to a gel intended for the analysis of proteins.

After migration, the gel is fixed, dried and stained with Ponceau red according to the usual procedures.

EXAMPLE 2

PROTEIN ANALYSIS OF A SERUM INVOLVING STAINING WITH AMIDO BLACK

The procedure is as indicated in example 1, except that the exposure time is reduced to two minutes and the application time to 30 seconds.

After migration, the gel is fixed, dried and stained with Amido Black according to the usual procedures.

EXAMPLE 3

PROTEIN ANALYSIS OF A SERUM INVOLVING STAINING WITH ACID VIOLET

The procedure is as indicated in example 1, except that the exposure time is reduced to two minutes and the application time to fifteen seconds.

After migration, the gel is fixed, dried and stained with Acid Violet according to the usual procedures.

EXAMPLE 4

HIGH RESOLUTION PROTEIN ANALYSIS OF A SERUM

A porous membrane of cellulose acetate, having pore dimensions of 1.2μ and a thickness of 100μ, is used which comprises four projecting elements 7 mm in diameter and separated from each other by 3 mm, this membrane being attached to a rigid support (cf. FIG. 5).

By means of a micropipette, one drop of 5μ l of each of four samples to be analysed separated by 10 mm from each other are loaded onto parafilm in a straight line.

The free ends of the projecting elements are simultaneously placed in contact with the various samples until the front of the liquid samples has been absorbed into the projecting elements to a height of 3 mm from the end.

The spongy material is then impregnated with 1 ml of humidification liquid consisting of a 10% aqueous solution of Dextran of molecular mass $5\times10^5$ by means of a pipette.

After a waiting period of 5 minutes the apparatus is applied for 30 seconds to a gel intended for high resolution analysis of proteins.

After migration, fixation and drying, the gel is stained with Acid Violet according to the usual procedures.

EXAMPLE 5

PROTEIN ANALYSIS OF A SERUM INVOLVING STAINING WITH AMIDO BLACK

A porous membrane of cellulose acetate, having a pore size of 0.45µ, a thickness of 130µ and impregnated with 2% of 1,3-butanediol, is used which comprises eight projecting elements 3 mm in diameter separated from each other by 1.5 mm, and attached to a rigid support (in conformity with the diagram shown in FIG. 2).

By means of a micropipette, 1 µl of each sample is loaded close to the end of each projecting element.

The reservoir (D) constituted by the rigid support (B), on the one hand, and by the porous membrane (A), on the other, is loaded with 200 µl of physiological water.

After exposure to air for 2 minutes the apparatus is applied for 1 minute to a gel intended for the analysis of proteins.

After migration, the gel is fixed in a stream of air heated to 70° C. and stained with Amido Black according to the usual procedures.

EXAMPLE 6

PROTEIN ANALYSIS OF A SERUM INVOLVING STAINING WITH PONCEAU RED

A porous membrane of nylon, having a pore size of 0.45µ and a thickness of 120µ, is used which comprises six projecting elements 4 mm in diameter and separated from each other by 2 mm, this membrane is supported on a stiffening support (in conformity with the diagram shown in FIG. 4).

By means of a micropipette, 1µ of each sample is loaded close to the end of each projecting element.

The reservoir (D), constituted by the elements (B) and (C) of the rigid support, on the one hand, and by the flexible magnetic elements (J) and (H), on the other, is loaded with 100 µl of water by means of a pipette.

The entire apparatus and, in particular, the ends of the projecting elements extending beyond the stiffening system, is placed for 2 minutes in a current of air at room temperature before being applied for 1 minute to an agarose gel intended for the separation of proteins.

After migration, the gel is fixed, dried and stained with Ponceau red according to the usual procedures.

EXAMPLE 7

LIPID ANALYSIS OF A SERUM ON AGAROSE GEL: STAINING WITH SUDAN BLACK

A porous membrane of cellulose acetate, having a pore size of 8µ and a thickness of 140µ, is used which comprises six projecting elements 4 mm in diameter separated from each other by 2 mm, this membrane is attached to a stiffening support (in conformity with the diagram shown in FIG. 3).

By means of a micropipette, 1 µl of each sample is loaded close to the ends of the projecting elements.

The reservoir, constituted by the rigid support (D), on the one hand, and the flexible flap (F), inclined at about 45°, on the other, is loaded by means of a pipette with 100 µl of humidification liquid constituted by a 1% solution of hydroxyethylcellulose of molecular weight $5.10^5$.

After exposure to air for 10 minutes, the apparatus is applied for 2 minutes to a gel intended for the separation of lipoproteins.

After being dried in a stream of warm air, the gel is stained with Sudan Black according to the usual procedures.

EXAMPLE 8

ANALYSIS OF THE ISOENZYMES OF LACTATE DEHYDROGENASE (LDH)

The procedure is as indicated in example 6, except that the time of exposure is reduced to 6 minutes.

The apparatus is then applied for 2 minutes to an agarose gel intended for the separation of the isoenzymes of the LDH.

After migration, the gel is immediately stained by means of the usual substrates according to standard procedures.

EXAMPLE 9

DETECTION AND IDENTIFICATION OF THE PARAPROTEINS BY IMMUNOFIXATION

A porous membrane of cellulose acetate, having a pore size of 8µ and a thickness of 140µ, is used which comprises a single projecting element 40 mm in diameter attached to a stiffening support (in conformity with the diagram shown in FIG. 3).

By means of a micropipette, and close to the end of the projecting element and along the entire length of this element, is deposited the sample previously diluted ⅕ in physiological water so that it spreads to a height of about 5 mm measured from the end of the projecting element.

The reservoir, constituted by the rigid support (B), on the one hand, and the flexible flap (F) inclined at about 45°, on the other, is loaded with 100 µl of humidification liquid constituted of a 0.25% aqueous solution of polyacrylamide of molecular mass $5\cdot10^6$.

After a waiting period of 2 minutes, the apparatus is applied for 30 seconds to a gel intended for immunofixation analyses.

After migration, the gel is treated according to the usual procedures of immunofixation.

EXAMPLE 10

DETECTION AND IDENTIFICATION OF THE PARAPROTEINS BY IMMUNOFIXATION

The procedure is as indicated in example 8, up to the end of the migration step.

The loading of the antisera performed previously with a mask is replaced by loadings carried out by means of the same approach as that used for the loading of the sample, namely:

five porous membranes of cellulose acetate, having a pore size of 8μ and a thickness of 140μ, are used, each of which comprises a single projecting element 40 mm in diameter, which is attached to a stiffening support (in conformity with the diagram shown in FIG. 3).

By means of a micropipette, each of the anti-IgG, anti-IgA, anti-IgM, anti-kappa and anti-lambda antisera are loaded onto each of the five porous membranes close to the ends of the projecting elements and over a height of about 5 mm.

Each of the five reservoirs is loaded with 100 μl of humidification liquid constituted by a 0.25% solution of polyacrylamide of molecular mass $5\times10^6$.

After a waiting period of 2 minutes the five porous membranes are simultaneously applied (for 2 minutes), perpendicularly to the initial loading of the sample and at 5 mm from each other.

Incubation is allowed to proceed for 10 minutes and the remainder of the procedure is as in example 8.

EXAMPLE 11

ANALYSIS OF THE PROTEINS IN A URINE

A porous membrane of cellulose acetate, having a pore size of 8μ and a thickness of 140μ, is used which comprises four projecting elements 6 mm in diameter separated from each other by 3 mm, and the membrane is attached to a stiffening support (cf. FIG. 5).

By means of a micropipette, 6 μl of sample are loaded close to the end of each projecting element, the front of the sample being at a distance of about 7 mm from the ends of the projecting elements.

The humidification liquid is supplied by a 1% agarose gel 1 mm thick (cf. FIG. 5, part L containing a 0.05M sodium bicarbonate-carbonate buffer, pH 10.5).

The entire apparatus, and in particular the ends of the projecting elements extending beyond the stiffening system, is placed in a current of air for 3 minutes at room temperature, the time necessary for the sample front to become situated at 0.5 mm from the end of the projecting elements.

The upper end of the element L (agarose gel) is then connected to the positive pole of a generator, and the positive pole of the generator is connected to the bottom of the electrophoresis gel, the end furthest away from the side of application.

The application to an agarose-7% acrylamide gel is performed at a voltage of 300 V for 1 minute.

After the application, the end of the electrophoresis gel situated close to the side of application (the top) is connected to the negative pole of the generator and migration is allowed to continue.

After migration, the gel is stained with Coomassie Blue according to the usual procedures.

EXAMPLE 12

PROTEIN ANALYSIS OF A SERUM INVOLVING STAINING WITH ACID VIOLET

An apparatus of the invention is used which comprises four independent projecting elements made of a porous material (cellulose acetate), having pore dimensions of 1.2μ and a thickness of 100μ, these projecting elements being rectangular, 12 mm high and 7 mm wide, separated from each other by 2 mm and glued to a rigid support (cf. FIG. 6).

A strip of hydrophobic paper N is glued across the middle of the projection elements.

The entire apparatus is placed in a horizontal position and by means of a pipette 15 μl of sample are loaded per projecting element on the area of the projecting element situated above the strip N and remote from the end which is subsequently applied to the gel.

After a waiting period of about 1 minute, the sample has reached the end by capillary diffusion in the porous membrane.

After an additional waiting period of 2 minutes for the purpose of concentration by evaporation in air, the apparatus is applied for 20 seconds to an agarose gel intended for the analysis of proteins.

After migration, the gel is fixed, dried and stained with Acid Violet according to the usual procedures.

EXAMPLE 13

PROTEIN ANALYSIS OF A SERUM INVOLVING STAINING WITH AMIDO BLACK

A porous membrane of cellulose acetate, having pore dimensions of 8μ and a thickness of 140μ, is used.

The apparatus of the invention comprises four independent projecting elements (made of porous material), in the form of a square of size 7 mm, separated from each other by 2 mm, each projecting element being coated with a coating of a plastic film 10μ thick, except for the lower transverse section of the projecting element and for an area mm high situated in the proximity of the upper transverse section (cf. FIG. 7).

The apparatus is placed in the horizontal position and by means of a pipette 12μ of sample are loaded onto the zone uncoated by the plastic coating.

After about 30 seconds, the sample liquid has reached the end of the porous elements by means of capillarity.

The apparatus is then applied for 30 seconds to an agarose gel intended for the analysis of proteins by electrophoresis.

After migration, the gel is fixed, dried and stained with Amido Black according to the usual procedures.

I claim:

1. Procedure for loading of one or several biological samples on an electrophoretic slab support, comprising the steps of:

loading the one or several biological samples onto one or more projecting elements made of porous material and joined to an edge of a planar porous membrane and as an extension in a same plane of said planar porous membrane, the loading of the one or several biological samples being performed at a free end of the one or more projecting elements, the one or more projecting elements being such that they all have at least one point capable of being placed in contact with a planar surface of the electrophoretic slab support, different points being simultaneously placed in contact with the planar surface of the electrophoretic slab support as a result of an alignment, when the planar porous membrane is arranged in an inclined or perpendicular plane with respect to the planar surface of the electrophoretic slab support, wherein at least a part of the planar porous membrane is attached to a stiffening support, wherein diffusion of the one or several biological samples from the free end of the one or more projecting elements towards the planar porous membrane is avoided with an aid of agents for humidification of the one or more projecting elements, the agents comprising a humidification liquid which, as a consequence of an evaporation of liquid from the one or several biological samples, creates a flux from the planar porous membrane towards the free end of the one or more projecting elements and forces the one or several biological samples towards the free end of the one or more projecting elements, and which concentrates the one or several biological samples at the free end, the agents comprising a spongy material attached in a removable or irremovable manner to the planar porous membrane or to the stiffening support or a reservoir attached in a removable or irremovable manner to the stiffening support; and placing in contact the one or more projecting elements of the planar porous membrane, a part of which is attached to the stiffening support with the electrophoretic slab support in order to cause diffusion of the one or several biological samples from the one or more projecting elements onto the electrophoretic slab support and to thus load the one or several biological samples onto the electrophoretic slab support.

2. Procedure according to claim 1, wherein the diffusion of the one or several biological samples from the free end of the one or more projecting elements towards the planar porous membrane is prevented before or after attachment of a part of the one or more projecting elements of the planar porous membrane to the stiffening support.

3. Procedure according to claim 2, wherein the diffusion of the one or several biological samples and concentration towards the free end of the one or more projecting elements is caused by creating a flux of humidification liquid by evaporation of the humidification liquid of the one or several biological samples, or by accelerating the evaporation and flux by a current of air at a temperature lower than or equal to 40° C.

4. Procedure for loading a biological sample comprising the steps of:

loading of a biological sample according to claim 1, onto a slab support with an aid of projecting elements, the loading not being followed by electrophoresis;

loading of a reagent in a direction perpendicular to a previous load and intersecting the previous load;

incubating said biological sample with said reagent; and revealing a result of a reaction possibly formed between the biological sample and the reagent.

5. Procedure for loading a biological sample comprising the steps of:

loading a biological sample according to claim 1, allowing an electrophoretic migration to take place;

loading a reagent in a direction approximately perpendicular to a first loading over a distance;

encompassing an entire distance of the electrophoretic migration when the electrophoretic migration is complete;

allowing incubation to proceed; and revealing a result of a reaction formed between the biological sample and the reagent.

6. Procedure for loading one or several biological samples onto an electrophoretic slab support, comprising the steps of:

loading the one or several biological samples onto one or more independent planar elements, made of porous material, attached to common stiffening devices, which maintains the one or more independent planar elements in a same plane, the one or more independent planar elements projecting beyond the common stiffening devices as projecting elements, each of the projecting elements comprising:

two surfaces, one of which is at least in part supported by the common stiffening devices wherein one of the two surfaces of each of the projecting elements is fitted with a strip placed in a vicinity of a central part of the each of the projecting elements and attached to at least a part of the surface of the each of the projecting elements which is a reverse of the surface of which a part at least is supported by the common stiffening devices, thus dividing the each of the projecting elements into an upper part and a lower part, a size of the strip varying from one fifth to a whole of one of the two surfaces of the each of the projecting elements, two longitudinal sections, two ends corresponding approximately to transverse sections, one of the transverse sections being designed to be applied to the electrophoretic slab support and being designated as a lower transversal section and the other one of the transverse sections opposite to the lower transversal section and designated as an upper transversal section, the common stiffening devices being such that form and dimensions are compatible with form and dimensions of the projecting elements, to support a part of the projecting elements by the common stiffening devices under conditions such that the common stiffening devices do not hinder placing in contact of the projecting elements with planar surface of the electrophoretic slab support and the loading of the one or several biological samples on the electrophoretic slab support, each of the projecting elements comprising means which prevent a biological sample loaded onto one of the projecting elements to spread over the surface of the projecting elements, and/or to seep over the surface of the projecting elements, the projecting elements having at least one point of contact with the surface of the electrophoretic slab support, different points being placed simultaneously in contact with the planar surface of the electrophoretic slab support as a result of an alignment when the common stiffening devices are arranged in an inclined or perpendicular plane with respect to the planar surface of the electrophoretic slab support, and placing in contact the projecting elements attached to the common stiffening devices with the electrophoretic slab support wherein the one or several biological samples is loaded in excess onto an upper part of the projecting element in a vicinity of the upper transversal section, the one or several biological samples thus loaded does not spread over the surface of the projecting element, diffuses to an interior of the projecting element and reaches the lower transversal section of the projecting element in order to be loaded onto the electrophoretic slab support.

7. Procedure according to claim 6, wherein each projecting element is coated with a hydrophobic material on both its surfaces, and on the two longitudinal sections, the hydrophobic material being such that the hydrophobic material recovers 20% to 100% of the two surfaces upwards from the lower transversal section, to an extent of 100% of a surface supported by the stiffening devices and from 20% to 100% of a reverse surface, and hydrophobic coats a whole of the two surfaces with an exception of the two transverse sections, wherein a biological sample is loaded in excess in the vicinity of the upper transversal section of the projecting element which is not coated by the hydrophobic material, and since the biological sample diffuses longitudinally into an interior of a hydrophobic film until the biological sample reaches the lower transversal section of the projecting element which is not coated, the loading of the biological sample onto the electrophoretic slab support is achieved by capillary action.

8. An apparatus for an application of biological samples to an electrophoretic slab support, comprising:

(a) a planar porous membrane including on one of edges one or more projecting elements made of porous material said projecting elements being partially joined to said planar porous membrane and lying in a same plane as said planar porous membrane wherein a part of the projecting elements not joined to the planar porous membrane has a free end;

(b) at least one stiffening device attached to said one or more projecting elements wherein the stiffening device maintains in the same plane as said one or more projecting elements; and (c) means for humidificating said one or more projecting elements, said humidification means being separable or inseparable from said planar porous membrane.

9. The apparatus according to claim 8, wherein said one or more projecting elements are resting on an edge of a planar porous membrane, joined to the planar porous membrane, extending in the same plane as the planar porous membrane and acting as a projection of the planar porous membrane as the one or more projecting elements wherein a projecting part of the one or more projecting elements not joined to the planar porous membrane has a full end, the planar porous membrane and the one or more projecting elements having a thickness of 50µ to 200µ.

10. The apparatus according to claim 9, wherein said one or more projecting elements have a thickness of 100µ to 150µ.

11. The apparatus according to claim 8, wherein said one or more projecting elements are independent of each other.

12. The apparatus according to claim 8, wherein the planar porous membrane and the one or more projecting elements are a same porous material, the one or more projecting elements being cut from one of the edges of the planar porous membrane.

13. The apparatus according to claim 12, wherein said planar porous membrane and said one or more projecting elements have a thickness of 50µ to 200µ.

14. The apparatus according to claim 13, wherein said planar porous membrane and said one or more projecting elements have a thickness of 100µ to 150µ.

15. The apparatus according to claim 8, wherein said one or more projecting elements are separated, square or rectangular strips.

16. The apparatus according to claim 15, wherein said strips are separated by a distance of at least 0.5 mm.

17. The apparatus according to claim 8, wherein said means for humidificating is a material impregnated with a humidification liquid.

18. The apparatus according to claim 17, wherein said material impregnated with said humidification liquid is a spongy material.

19. The apparatus according to claim 8, wherein said planar porous material is a hydrophilic material selected from a group of cellulose, a cellulose ester, cellulose acetate, cellulose proprionate, cellulose nitrate, mixed esters of cellulose nylon and derivatives thereof.

20. The apparatus according to claim 8, wherein said planar porous material is a hydrophobic material selected from a group of polyethylene, polypropylene, polycarbonate and derivatives thereof.

21. The apparatus according to claim 8, wherein said means for humidificating is a reservoir integrated into said stiffening device or detachable from said stiffening device.

22. The apparatus according to claim 8, wherein said planar porous membrane is a sheet of cellulose acetate, rectangular or square and the one or more projecting elements are strips separated from each other and situated on one side of the planar porous membrane.

23. The apparatus according to claim 8, wherein said planar porous membrane is a sheet of paper and the one or more projecting elements are separated from each other and situated on one side of the planar porous membrane.

24. The apparatus according to claim 8, wherein attached to at least part of the surface of each of the one or more projecting element is a hydrophobic material.

25. The apparatus according to claim 24, wherein said hydrophobic material further contains a wetting agent of glycerol, 1,3-butane dial or uncharged surfactants at concentrations from 0.001% to 10%.

* * * * *

UNITED STATES PATENT AND TRADEMARK OFFICE
CERTIFICATE OF CORRECTION

PATENT NO. : 5,464,515

DATED : November 7, 1995

INVENTOR(S) : Bellon

It is certified that error appears in the above-identified patent and that said Letters Patent is hereby corrected as shown below:

Delete colums 1- 28, and substitute columns 1-28 per attached

Signed and Sealed this

Tenth Day of June, 1997

Attest:

BRUCE LEHMAN

Attesting Officer    Commissioner of Patents and Trademarks

This is a continuation of application Ser. No. 07/811,174, filed Dec. 19, 1991, now abandoned.

BACKGROUND OF THE INVENTION

The object of the invention is to provide an apparatus for the application of biological samples to an electrophoretic slab support and, advantageously to an electrophoresis gel.

The purpose of the procedure of zone electrophoresis on agarose gel is to fractionate the protein constituents of a biological sample such as serum, urine, cerebrospinal fluid, etc, by subjecting them to the action of an electric field in a gel medium containing a buffer solution. At a specified, usually basic pH the proteins, which are amphoteric molecules, ionize and are separated according to their respective charges. The fineness of the bands obtained after electrophoresis and hence the resolving power of the procedure depend mainly on how fine the sample is loaded onto the gel.

In fact, in isoelectric focusing, in isotachopheresis or in acrylamide gradient electrophoresis or even in acrylamide gel electrophoresis (by the use of a "stacking gel"), it is possible to obtain a focusing of the fractions by the electrophoresis itself. In zone electrophoresis, for example, on agarose gel alone, a very fine loading of the sample onto the gel makes it possible to produce highly focused fractions.

In order to load the sample for the purpose of electrophoresis, it is possible to use combs made of plastic material, the teeth of which contain a groove which makes it possible to recover a drop of biological sample having a volume of about 0.3 to 2 μL. However, the drop may be of a dimension such that it usually does not allow a sufficiently fine loading and, depending on the type of analysis, it is sometimes necessary to carry out a prior dilution of the sample to be analyzed, in order to prevent loading the sample in too large amounts.

In order to load the sample for the purpose of electrophoresis, it is also possible to use a loading mask with fine slots (about 0.3 to about 0.5 mm) which make it possible to produce good focusing of the loading which is necessary for a satisfactory image. Nonetheless, the use of this mask to load the samples through the slots is difficult to automate. Moreover, the "automatic" applicators presently available do not enable a fine sample loading to be obtained equivalent to that produced with manual loading performed through the fine slots of the mask.

Furthermore, on account of the relatively large size of the drops, quite wide bands are obtained which makes the separation of the proteins difficult.

In the case of an agarose gel, it is also possible to use moulded gels containing wells and, in this case, the syringe which is used to load the sample must be directed very carefully into the well. Loading the sample is usually done successfully if the size of the wells is sufficiently large. Thus, in the case of a well having a width greater than or equal to about 1 mm, the apparatus can be automated but the resolution is inadequate. If the size of the wells is sufficiently small to give good resolution, then the apparatus cannot be automated.

OBJECTS AND SUMMARY OF THE INVENTION

The object of the invention is to find a solution to these disadvantages by providing an apparatus for the application of biological samples which, on the one hand, makes it possible to obtain a very fine loading of the sample sufficient to give high resolution and, on the other, can be automated and which ultimately enables variable amounts of sample to be loaded (quite considerable amounts of sample which can be varied as desired).

Yet another object of the invention is also to provide an apparatus for the application of biological samples at a moderate price.

The object of the invention is an apparatus for the application of biological samples to an electrophoretic slab support, in particular an electrophoresis gel, characterized in that it comprises one or more planar elements made of porous material on which a biological sample can be loaded. These planar elements can be either resting on the edge of a planar porous membrane, joined to the porous membrane, extending in the same plane as the latter and act as a projection of the porous membrane. These elements being designated hereafter as "projecting elements". The projecting part of these elements not joined to the porous membrane has a free end. Furthermore, the projecting elements may be independent of each other and are attached to common stiffening devices which maintain in the same plane, these elements projecting out from the stiffening devices. The stiffening devices being such that their form and their dimensions are compatible with those of the projecting elements to support one part of each projecting element under conditions such that the stiffening devices do not hinder the placing in contact of the projecting elements with the plane surface of the electrophoretic slab support and the loading of the biological sample onto the electrophoretic slab support.

Each of the projecting elements comprises means for the partitioning and/or retention of the biological sample which prevent a biological sample loaded onto one of the above-mentioned projecting elements from spreading over the surface of the said projecting element, and/or seeping out over the surface of the said projecting element without preventing the loaded biological sample from diffusing right to the end of the said projecting element. The projecting elements have at least one point capable of being placed in contact with the planar surface of the electrophoretic slab support in order that one or more biological samples can be loaded onto the said support, each biological sample being loaded beforehand onto one element of the projecting elements. These different points are simultaneously placed in contact with the surface of the slab support as a result of an alignment, when the porous membrane or the above-mentioned stiffening devices are arranged in an inclined or perpendicular plane with respect to the surface of the slab support.

BRIEF DESCRIPTION OF THE DRAWINGS

FIG. 1 is a plan-view and cross-view of one of the embodiments of the apparatus of the present invention which includes two rigid support elements (B and C), a rectangular porous planar membrane in which one of the membrane's edges comprises a rectangular projecting element (A) and a reservoir (D).

FIG. 2 is a plan-view and cross-view of an embodiment of the apparatus of the present invention including a rectangular porous planar membrane in which one of the membrane's edges comprises a rectangular projecting element (A), a single rigid support element (B) and a reservoir (D).

FIG. 3 is a plan-view and cross-view of an embodiment of the apparatus of the present invention including a rectangular porous planar membrane in which one of the membrane's edges comprises a rectangular projecting element (A), a single rigid support element (B), a reservoir (D) and a sheet of flexible hydrophobic material (F).

FIG. 4 is a plan-view and a cross-view of an embodiment of the present invention including a rectangular porous planar membrane in which one of the membrane's edges comprises a rectangular projecting element (A) fitted with a flexible magnetized material (J) which is itself fitted against one of the two elements of a rigid support (B). The support element (C) also has attached flexible magnetized material (H) and acts as clamp. The closed arrow indicates the form adopted by the clamp in a closed position.

FIG. 5 is a plan-view and a cross-view of an embodiment of the present invention including a rectangular porous planar membrane in which one of the membrane's edges comprises a rectangular projecting element (A), a single rigid support element (B) and a spongy material (L) attached to the surface of the porous membrane not fitted to the support.

FIG. 6 is a plan-view and a cross-view of an embodiment of the present invention including a rectangular porous planar membrane in which one of the membrane's edges comprises a rectangular projecting element (A), a single rigid support element (B) and a strip (N) made of hydrophobic material which is applied in the median part of the projecting elements.

FIG. 7 is a plan-view and a cross-view of an embodiment of the present invention including a rectangular porous planar membrane in which one of the membrane's edges comprises a rectangular projecting element (A) coated with a hydrophobic coating (P) and a single rigid support element (B).

FIG. 8 is a plan-view and cross-view of an embodiment of the apparatus of the present invention including a rectangular porous planar membrane which is bent at a 45 degree angle in which one of the membrane's edges comprises a rectangular projecting element (A), a single rigid support element (B) and a reservoir (D).

FIG. 9 is a plan-view and a cross-view of an embodiment of the present invention including a rectangular porous planar membrane in which one of the membrane's edges comprises a rectangular projecting element (A), a single rigid support element (B) which possesses an opening (E) and a reservoir (D) which is constituted by the lower horizontal part of the opening (E) in the support (B) and by part of the element (A).

FIG. 10 is a plan-view and a cross-view of an embodiment of the present invention including a rectangular porous planar membrane in which one of the membrane's edges comprises a rectangular projecting element (A), a single rigid support element (B) which possesses a reservoir (D) situated behind each of the projecting elements (A).

DESCRIPTION OF THE PREFERRED EMBODIMENTS OF THE INVENTION

The apparatus of the invention and the various embodiments of this apparatus makes it possible to load biological samples; in particular, onto an agarose or acrylamide gel or onto a membrane cellulose acetate.

The porous membrane and the projecting elements advantageously have a thickness of about 50μ to about 200μ, and preferably of about 100μ to about 150μ.

The apparatus of the invention makes it possible to load a biological sample without liquid transfer but by diffusion between two solid media which are, respectively, all of the projecting elements and the electrophoretic slab support, each being saturated with liquid in order to prevent transfer from one to the other. Under these conditions, very fine loading of the sample can be obtained, particularly if the zone of contact between the end of the projecting elements (i.e., the cross-section of the projecting elements) and the slab support are very small.

The apparatus for the application of biological samples is preferably designed for the application of the samples onto an electrophoresis gel.

The biological sample is constituted by a solution containing components to be determined. As examples, mention may be made of serum, urine, etc . . .

According to an advantageous embodiment, the apparatus of the present invention is represented in FIG. 1.

Figure 1A:
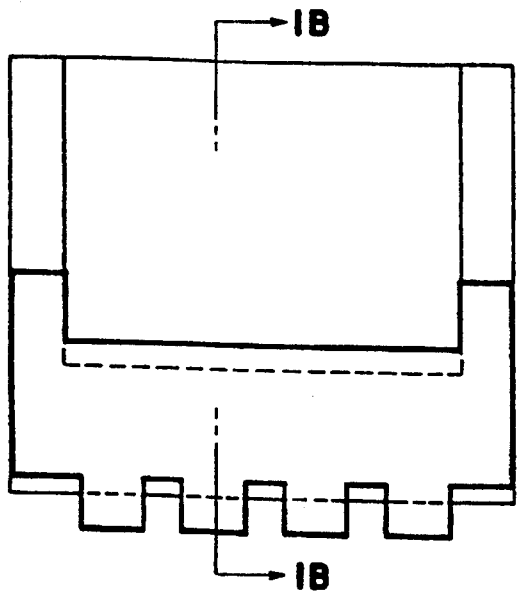
FIG. 1 represents a plan view and a cross-section view of an apparatus of the invention comprising a rectangular, porous, planar membrane (A) and in which one of the edges comprises rectangular projecting elements, and the edge of the membrane opposite to the projecting elements comprises a perpendicular extension on each side of the edge which gives to this side of the membrane the form of a U consisting of a linear horizontal part flanked on either side by a perpendicular projection. The membrane is inserted between the two elements (B and C) of a rigid support which are, for example, glued (in order to ensure impermeability between the stiffening support and the porous membrane) to the area to which the porous membrane has just been fitted and which open outwards in the proximity of the linear horizontal part but remain plated to the two perpendicular extensions of the porous membrane and are extended beyond them.

FIG. 1 represents a plan view and cross section view of the apparatus according to the present invention. This apparatus comprises at least one rectangular porous membrane containing at least one projecting element at one of its edges (FIG. 1(A)) and at the opposite edge of the projecting element a perpendicular extension of the membrane forms a U consisting of a linear horizontal part flanked on either side by a perpendicular projection. The porous membrane is inserted between two elements of a stiffening support (FIG. 1(B and C)), for example by gluing the porous membrane to said stiffening support. The area to which the stiffening devices have been attached opens outward in proximity, horizontally, but remains fixed to the two perpendicular extensions of the porous membrane and extends beyond them. The space formed by the outward opening of the stiffening supporting elements (FIG. 1(B and C)) from the porous membrane forms a reservoir (FIG. 1(D)).

Figure 1B:
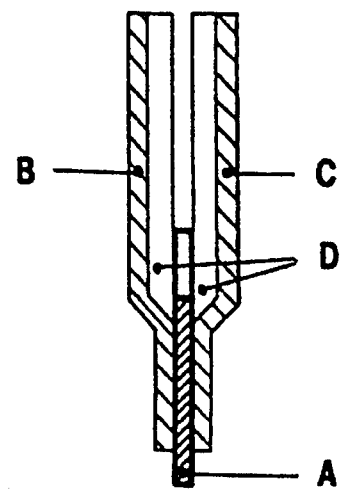
Figure 2A:
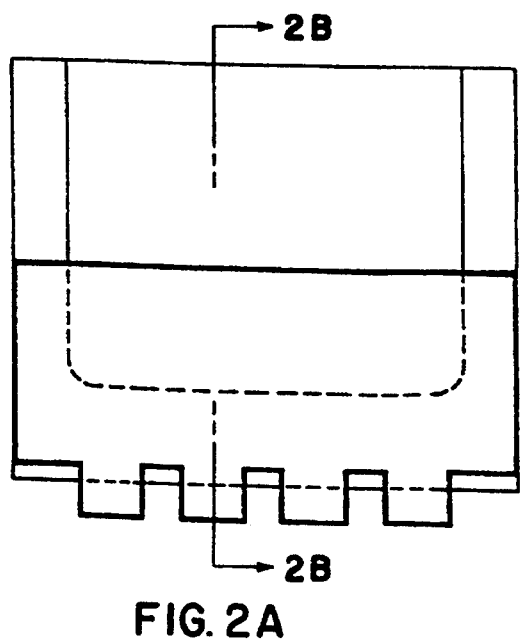
Figure 2B:
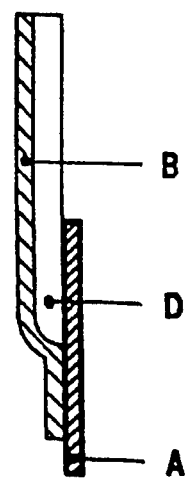

Three alternate embodiments of the apparatus depicted in FIG. 1 of the present invention are illustrated in FIGS. 2, 3 and 8, respectively. In FIG. 2 only one supporting element (FIG. 2(B)) having at least one rectangular, planar, porous membrane containing at least one projecting element (FIG. 2(A)) is attached to one side of the porous membrane. The supporting element (FIG. 2(B)) possesses a part which opens outward from the porous membrane thus forming a reservoir (FIG. 2(D)).

Figure 8A:
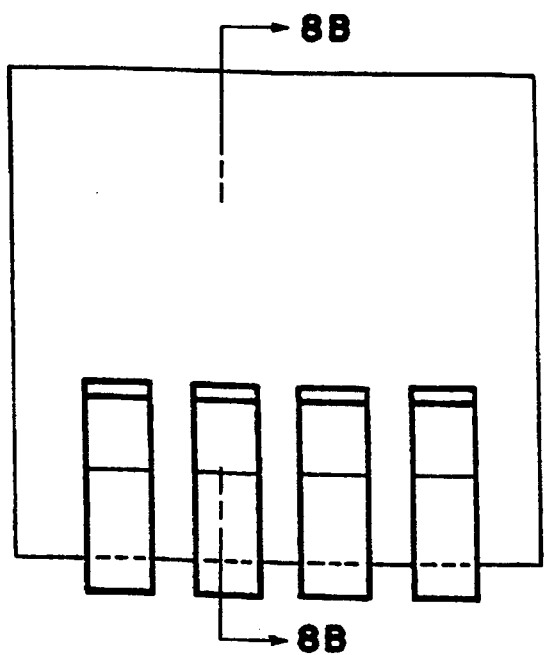
Figure 8B:
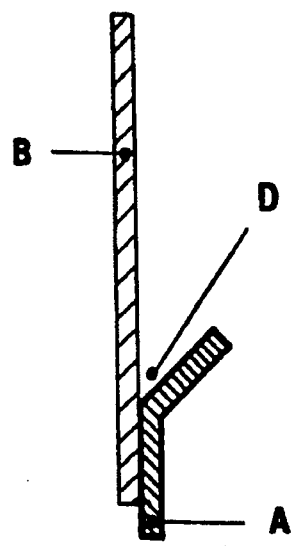

Similarly, FIG. 8 depicts the same porous membrane containing at least one projecting element (FIG. 8(A)) which is glued to a stiffening support (FIG. 8(B)) maintained in the same plane as the porous membrane. However, that part of the porous membrane which is not glued to the stiffening support (FIG. 8(B)) is bent at a 45 degree angle, thus creating a space between the porous membrane and the stiffening support (FIG. 8(B)) which forms a reservoir (FIG. 8(D)).

Instead of having an angled porous element, a sheet of flexible and hydrophobic material, for example paper, can be attached to the porous membrane in the vicinity of the upper edge of the porous membrane (FIG. 3(F)). This sheet (FIG. 3(F)) is also bent at a 45 degree angle, thus creating a space between the porous membrane and the stiffening support (FIG. 3(B)) which opens outward forming a reservoir (FIG. 3(D)).

Thus, these various embodiments of the apparatus of the invention comprise a porous membrane, the pores of which can absorb the sample and can, if necessary, also absorb a humidification liquid.

According to an advantageous embodiment, the apparatus of the invention comprises means for the humidification of the projecting parts, which are depicted as (D) is FIGS. 1 to 4, 8, 9 and 10, and (L) in FIG. 5, whether separable or not from the above-mentioned porous membrane.

The humidification liquid is incorporated into the porous membrane, above the front of the biological sample. If the humidification liquid is introduced into the porous membrane at least to saturation and preferably in excess with respect to the absorption capacity of the porous membrane, it migrates by capillary action to the level attained by the sample and it maintains the sample there where the latter is absorbed.

It may be said that the porous material is saturated with liquid if the total volume of its pores is occupied by liquid. Thus, a porous membrane with a degree of porosity of 60% is at saturation when it contains liquid corresponding to 60% of its volume and a porous membrane with a degree of porosity of 90% is at saturation when the liquid it contains corresponds to 90% of its volume.

Furthermore, if evaporation of the solution containing the sample occurs, the humidification liquid which saturates the porous membrane and which is advantageously introduced in excess with respect to the absorption capacity of the porous membrane will replace the solvent of the sample solution which has evaporated, and which will return the sample towards the end of the projecting elements and lead to its concentration.

The presence of the humidification liquid in the membrane made of porous material creates a flux directed from the porous membrane towards the ends of the projecting elements which results in the biological sample being returned towards the respective ends of the projecting elements.

The biological sample, loaded preferably at the end of a projecting element, diffuses from the end of the projecting element upwards for a distance of about 1 to about 10 mm, in particular from about 3 mm to about 5 mm, the limit of this upward movement constituting a line of equilibrium between the diffusion of the sample and the reversal of flow created by the humidification liquid.

The biological sample, is absorbed by capillary action into the pores of the porous membrane up to a certain height (called "sample front") which depends on the volume loaded, the size of the projecting element, its thickness and the degree of porosity of the material of the projecting element. The sample front is situated at a distance, from the end of the projecting element, of 1 to 10 mm, in particular from about 3 mm to about 10 mm.

This distance also depends on the length of the projecting element, its thickness and the degree of porosity of the material of the projecting element.

When the distance of the sample front from the end of the projecting element is reduced as a consequence of flow reversal of the sample by the humidification liquid, the sample is concentrated. In an extreme case, the sample front may be situated after the concentration phase at a distance of 0.5 or 0.3 mm from the end of the projecting element which corresponds to a concentration of up to a factor of 20 or 30 in the case when the front is initially 10 mm high.

According to an advantageous embodiment of the invention, conditions are used such that the biological sample is concentrated at the end of the projecting elements since this makes it possible to use dilute biological samples without a prior concentration step.

In fact, the concentration of the sample takes place in the apparatus of the invention.

For example, the diffusion of the biological samples and their concentration towards the end of the projecting elements is brought about by accelerating the flux created by the humidification liquid, this flux being directed from the porous membrane towards the end of the projecting elements on which the biological samples are loaded, by, accelerated evaporation of the sample liquid by the use of a current of air either at room temperature or at a temperature preferably lower than or equal to about 40° C.

This concentration procedure may vary depending on the types of analysis envisaged. The concentration factor may vary from about 1.2 to about 3 in the case of protein analysis of serum; by a factor of about 2 to about 5 in the case of lipid analysis of serum; and by a factor of about 10 to about 30 in the case of analysis of proteins in urine or in cerebral-spinal fluid.

The volume of the biological sample loaded onto the electrophoresis gel varies from 0 to the total volume of the biological sample loaded onto the end of the projecting elements.

For degrees of porosity varying from about 50% to about 90%, the loading volume of a biological sample onto a projecting element varies from about $0.05 \times 10^{-2}$ to about $1 \times 10^{-2}$ µl/mm and per µ of thickness of the porous material, and preferably from about $0.15 \times 10^{-2}$ to about $0.5 \times 10^{-2}$ µl/mm and per µ of thickness of the porous material.

In the case of independent projecting elements, the amount of sample loaded is in excess with respect to the absorption capacity of the porous membrane. For example, in the case of a porous membrane element with a degree of porosity of 80%, and a surface area of 100 mm² and a thickness of 100 µ, the amount of sample loaded will be greater than $0.8 \times 100 \times 0.1$, i.e., greater than 8 µl.

In practice, an excess of 1.5 to 3 times the absorption capacity of the porous membrane element should be loaded. Beyond that there is a risk that the hydrophobic barrier can no longer play its role with running off of the sample drop loaded in excess to the end of the projecting element.

As far as the electrophoresis gel is concerned, this latter is always saturated with liquid since even if it undergoes partial dehydration, the pores collapse; i.e., there is a diminution of the volume of the pores which are nonetheless still occupied by liquid.

When the porous material is saturated with liquid the passage from the end of the projecting elements onto the gel of the known sample diluted in part of the volume (loaded onto the extremity of the projecting elements) thus occurs by diffusion and not by transfer of the solution.

When the porous material is not saturated with liquid, the transfer of liquid from the gel towards the porous material as a result of a capillary phenomenon, which counteracts the diffusion of these molecular species onto the gel occurs. This phenomenon is greater the further removed the porous material is from saturation.

It can be estimated that once the amount of liquid impregnating the porous material is less than or equal to 90% of the quantity of liquid impregnating it at saturation, no further loading can be effected.

For semantic reasons, the expression "amount of biological samples loaded onto the slab support or onto the gel" designates in the foregoing and in the following the amount of substances to be analyzed contained in part of the volume of the biological sample loaded onto the end of the projecting elements and which has diffused into the gel.

The amount of substances to be determined contained in part of the volume of the biological sample deposited on the electrophoresis gel must be present in the slab support or the gel in sufficient quantity for them to be detected and, the substances to be determined are not present in amounts greater than the amount above such that resolution becomes inadequate.

The amount of the substances to be analyzed, loaded onto the slab support or the gel it depends, on the time of flow reversal or concentration of the biological sample at the end of the projecting element and on the time of application from the end of the projecting element onto the slab support or onto the gel. It also depends on the substances to be analyzed.

As an example, in the case of the determination of proteins contained in serum, the amount to be loaded onto the gel may vary depending on the sensitivity of the stain used. The concentration time of the biological sample at the end of the projecting elements and the application time to the electrophoretic slab support may also vary as a function of the stains selected to reveal the proteins under invertigation.

In the case of a relatively insensitive stain such as Ponceau red, the phase of concentration by means of evaporation in air of the solution of the biological sample should be, for example, 5 minutes (sample concentrated about 1.8 fold) before loading with an application time to the gel of one minute. Under these conditions, the amount of substances to be analyzed loaded per mm is about 0.06 µl of the initial sample.

In the case of a more sensitive stain, for example, Amido Black, the phase of concentration by evaporation in air of the solution of the biological sample should be, for example, 2 minutes (sample concentrated about 1.3 fold) before loading with an application time to the gel of 30 seconds. Under these conditions, the amount of substance to be analyzed loaded per mm is about 0.02 µl of the initial sample.

In the case of an even more sensitive stain, for example Acid Violet, the phase of concentration by evaporation in air of the solution of the biological sample should be for example 2 minutes (sample concentrated about 1.3 fold) before loading with an application time to the gel of 15 seconds. Under these conditions, the amount of substance to be analyzed loaded per mm is about 0.01 µl of the initial sample.

In the case of a lipid analysis, the phase of concentration by evaporation in air of the solution of the biological sample should be, for example, 10 minutes (sample concentrated about 2.7 fold) before loading with an application time to the gel of about 2 minutes. Under these conditions, the amount of sample loaded per mm is about 0.12 µl of the initial sample.

In the case of the determination of LDH (lactate dehydrogenase) isoenzymes, the phase of concentration by evaporation in air of the solution of the biological sample should be for example 6 minutes (sample concentrated about 2 fold) before loading with an application time to the gel of 2 minutes. Under these conditions, the amount of sample loaded per mm is about 0.1 µl of the initial sample.

As for the porosity, it is defined by two parameters which are the degree of porosity, i.e., the ratio between the total volume of the interstices occupied by the pores and the total volume of the material, and the size of the pores.

The degree of porosity of the material varies from about 50% to about 90%.

The size of the pores varies from about 0.2 µ to about 20 µ, and advantageously from about 2 µ to about 10 µ, and most advantageously is about 8 µ.

If the pores are too small, flow reversal and possibly the concentration at the end of the projecting elements requires too long a time. If the pores are too large, the biological sample siphons through the pores (driven by the humidification liquid); in this latter case, transfer rather than diffusion takes place and there is loss of fine loading of the sample.

However, in order to prevent the siphoning phenomenon, it is possible to modify the viscosity of the humidification liquid, for example by using a polymer advantageously possessing the same properties as the polymers defined below with respect to the sharpness of the biological sample front.

The contact between the ends of the projecting elements and the slab support, occurs when the angle between the slab support and the ends of the projecting elements is about 45° to about 90°, and advantageously about 90°.

Concerning the humidification of the porous membrane, the humidification liquid may be deposited each time the device is used with the aid of any means for doing so, such as a pipette.

The humidification may take place either before (insofar as the front of the humidification liquid has not yet attained the zone where the loading of the sample must occur), or preferably after the loading of the sample onto the ends of the projecting elements.

When the projecting elements are placed in contact with the gel, it is not necessary that the liquid reserve due to humidification and hence the flow reversal of the biological sample (and possibly the concentration of the biological sample at the end of the projecting elements) is still present if loading the sample onto the gel follows immediately after the humidification phase or if loading the sample onto the gel follows immediately after humidification.

In the first stage, for example, it is possible to immerse the part opposite to the projecting elements in a humidification solution placed in a reservoir separate from the apparatus of the invention, then to immediately carry out placing the ends of the projecting elements thus treated in contact with the gel.

However, specific humidification means may be bound to the membrane in a reversible or irreversible manner. These humidification means may be composed of a material capable of receiving the humidification liquid (FIG. 5(L)) or consist of a reservoir. The reservoirs are depicted as (D) in FIGS. 1 to 4, 8, 9 and 10, and are capable of containing the humidification liquid.

In two other embodiments, the reservoir (D) is not in the form of a space opening outward between the porous membrane and the stiffening support but resides in the stiffening support (FIG. 9(B)) which possesses an opening (FIG. 9(E)) which may be rectangular wherein the upper part of the porous membrane is located by the opening. The reservoir (FIG. 9(D)) in which the sample is loaded is then constituted by the lower horizontal part of the opening (FIG. 9(E)) in the support (FIG. 9(B)) and by part of the porous membrane containing the projecting element which is not glued (FIG. 9(A)).

A similar type of reservoir is depicted in FIG. 10 in which the reservoir (FIG. 10(D)) is situated in the stiffening support (FIG. 10(B)) which contains an opening (FIG. 10(D)) that acts as the reservoir in which the sample is loaded. The porous membrane containing at least one projecting element is supported in part by the stiffening support (FIG. 10(B)) and is situated such that part of the porous membrane is behind the reservoir (FIG. 10(D)).

Instead of using a reservoir for the humidification liquid as depicted in FIGS. 1-3 and 8(D), a spongy material as illustrated in FIG. 5(L) may be used. In this embodiment, the porous planar membrane containing at least one protruding element (FIG. 5(A)) is attached to a solid support (FIG. 5(B)) and the spongy material is attached to the surface of the membrane not fitted to the support.

The spongy material may be (FIG. 5(L)) for example, a natural or synthetic sponge, or filter paper of adequate thickness, advantageously between about 0.5 mm and about 3 mm.

The spongy material capable of being impregnated with a humidification liquid may contain a quantity of liquid varying from about 2 fold to about 20 fold the weight of the said material. This material impregnated with humidification liquid may also be a gel, for example agarose gel.

According to an advantageous embodiment of the invention, the humidification means are situated above the area surrounding the front of each biological sample loaded onto each projecting element and advantageously above the parts of the porous membrane joined to the projecting elements.

The distance between the humidification means and the front of each sample varies from about 1 mm to about 20 mm, and is advantageously about 2 mm.

The humidification solution or agents may be water or an aqueous solution containing advantageously glycerol at concentrations of 0 to about 50% by volume, or a salt solution such as a solution of 0.15 M phosphate buffer, 0.15 M trisglycine buffer, 0.15 M citrate buffer or a solution containing NaCl, advantageously 0.15 M, etc . . .

The humidification solution advantageously contains a polymer making is possible to reduce the diffusion phenomena when the sample is returned towards the part of the porous membrane opposite the projecting elements.

Each projecting element is in contact with the gel over a length varying from 1 mm to about 200 mm, and preferably from about 1 mm to about 40 mm, depending on which biological sample is loaded on to the gel.

The porous membrane is quadrilateral in form, in particular, square or trapezoidal, and advantageously rectangular. One of the sides is joined to the projecting elements. The free end of the projection elements is, in particular, constituted by polygons such as triangles, trapezes, rectangles, squares, parts of a disc or parts of an ellipse.

The projecting elements are advantageously constituted by strips in the form of squares or rectangles, separated one from the other (FIG. 1 plan view).

Advantageously, these strips have a length of contact with the gel of about 1 to about 200 mm, in particular of about 1 to about 40 mm, and are separated from each other by a distance of at least about 0.5 mm.

The projecting elements are advantageously obtained by cutting them out from the porous membrane along one of its edges.

According to an advantageous embodiment of the invention, the porous membrane and the projecting elements are constituted by the same porous material.

The material of the porous membrane and the projecting elements are advantageously composed of hydrophilic material, such as cellulose or a cellulose derivative such as the cellulose esters (cellulose acetate, cellulose propionate, cellulose nitrate . . . ) or mixed esters of cellulose. The porous membrane may also be composed of nylon, or of a hydrophobic material such as polyethylene, polypropylene or polycarbonate.

Other porous materials which may be considered are regenerated cellulose, polyvinylidene fluoride, polysulfone or modified polysulfone. The porous membrane may also be composed of a cellulose acetate sheet or a sheet of paper.

To reduce the absorption time of the samples or of the humidification liquid in the pores of the porous membrane, either when the latter is insufficiently hydrophilic (for example, certain cellulose nitrates), or when it possesses a very small pore size (for example less than about $0.5\mu$) it is preferable, before using the porous membrane to incorporate a wetting agent of a type and in an amount that does not denature the components contained in the sample to be analyzed. This wetting agent is used in sufficient quantity in order that the sample loaded on each projecting element can penetrate by absorption into the porous material within a relatively short time of less than about 10 seconds. The wetting agent advantageously consists of glycerol, 1,3-butanediol or uncharged surfactants such as Triton X100 ® and Tween ®, used advantageously at concentrations between about 0.001% and about 10%.

The use of a wetting agent is particularly advantageous when the humidification means consist of a material capable of receiving the humidification liquid and capable of transferring the humidification liquid perpendicularly to the porous membrane. This is the case when the humidification agents are applied in a reversible or irreversible manner to the porous membrane, this application leading to the existence of zones which are not humidified, a circumstance which creates perturbations in the process of flow reversal of the biological sample towards the ends of the projecting elements.

However, when the humidification means consist of a reservoir, situated above the edge of the porous membrane, opposite to the projecting elements, it is possible not to use a wetting agent (in this case, the liquid is transferred in a parallel manner to the surface of the porous membrane).

The apparatus of the present invention also comprises stiffening devices for the porous membrane (FIGS. 1-10(B) and (C)) and/or agents for binding the porous membrane to a system of application of the biological samples which can be automated.

The stiffening devices for the porous membrane may be composed of a stiffening support for the porous membrane, the form and the dimensions of which are compatible with those of the porous membrane and those of the projecting elements, to maintain one part of the porous membrane by the stiffening support under conditions such that the support does not hinder either the placing in contact of the projecting elements joined to the porous membrane with the planar surface of the electrophoresis gel or the loading of the biological sample onto the electrophoresis gel.

The stiffening support may be composed of two elements between which a part of the membrane is inserted (FIG. 1(B) and (C)).

The binding agents may be constituted by a clamp (FIG. 4) or any technical equivalent capable of holding the porous membrane, if necessary stiffened by a support. The binding agents may confer on the membrane a suitable rigidity and be such that they are capable of comprising agents making it possible to constitute a reservoir capable of humidifying the porous membrane.

Figure 4A:
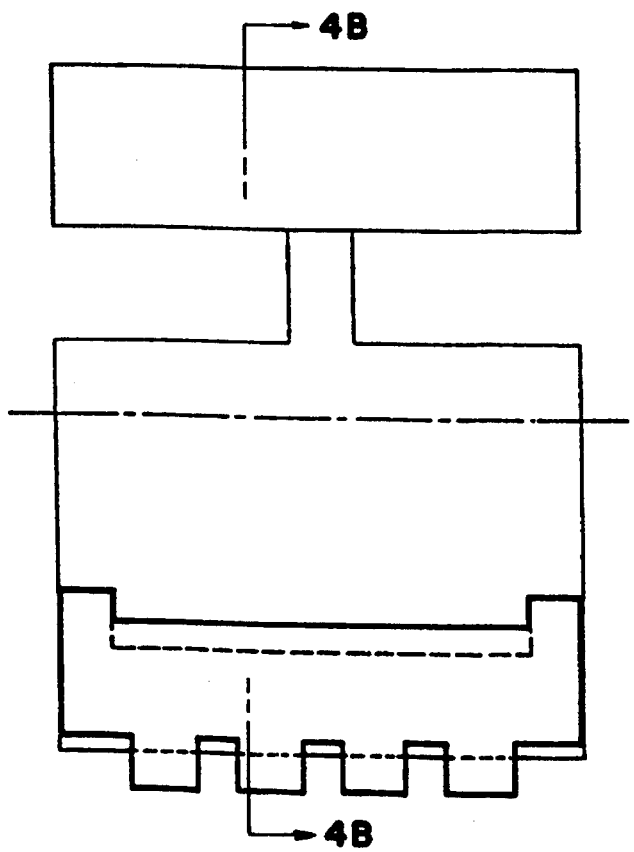
Figure 4B:
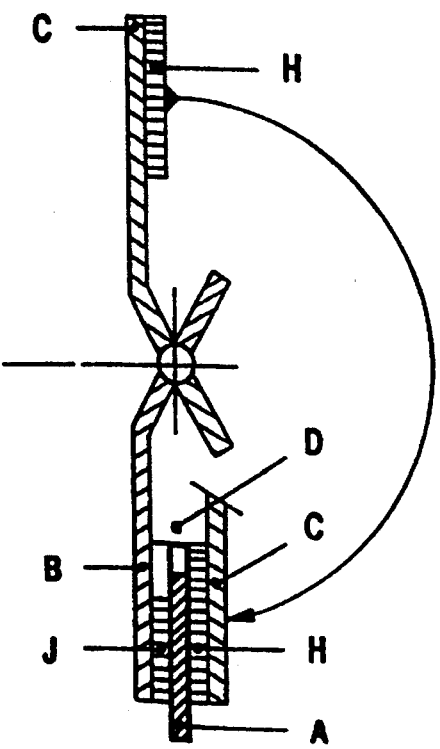

Another embodiment of the present invention is depicted in FIG. 4. FIG. 4 shows a plan view and a cross-section view of the apparatus of the present invention comprising a porous membrane having at least one projecting element (FIG. 4(A)) which is fitted against a flexible magnetic material (FIG. 4(J)), which has approximately the dimensions of the porous membrane. The flexible magnetized material (FIG. 4(J)), is fitted against one of the two elements of the solid support (FIG. 4(B)). The solid support (FIG. 4(B)) is articulated to the extent that it is capable of forming a clamp with the other solid support element (FIG. (C)). The support element (FIG. 4(B)) is rectangular in form and the support element (C) is in the form of a strip, which is articulated approximately in the middle of the upper part of the support element (B). A flexible magnetized material (FIG. 4(H)) which has approximately the same dimensions as the porous membrane is affixed to support element C (FIG. 4(C)).

In the cross-section view, the circular arrow indicates the form to be adopted by the clamp in a closed position. When the clamp is closed the porous membrane having a projecting element (FIG. 4(A)) is inserted and maintained between the magnetized materials of FIG. 4H and J, which are fitted to the support elements (FIG. 4(B) and (C)) respectively.

When the biological sample is loaded onto the end of the projecting parts, certain zones are impregnated before others by the biological sample, which may create an irregular front of the biological sample loaded onto the said projecting parts. In order to prevent these irregularities from becoming more pronounced during the concentration phase by the humidification solution, recourse is had to a polymer which, on account of its viscosity, has the function of ensuring the sharpness of the sample front, i.e., of making and maintaining the front of the biological sample approximately straight. In the case in which the projecting elements have the form of a rectangle, the role of the polymer is to make the front approximately parallel to the edge of the end of the said projecting elements.

Advantageously, the polymer used is a water-soluble polymer, of high molecular mass between about $2 \times 10^5$ and about $10^7$, such as hydroxyethylcellulose, dextran, polyacrylamide etc . . . at concentrations sufficient to ensure that the front of the sample loaded onto the projecting elements is approximately straight and at concentrations lower than that at which the humidification solution no longer diffuses owing to the breaking effect caused by the viscosity. The above-mentioned polymer advantageously has a concentration between about 0.05% and about 10%.

According to another embodiment of the invention, the porous membrane and the electrophoretic support include a pair of electrodes to create an electric field, after loading the biological sample onto the gel, between the porous membrane and the electrophoretic slab support. This field is capable of causing the biological samples to migrate from the projecting elements onto the slab support and thus load them onto the slab support.

Voltage is then applied to the electrophoretic slab support in order to cause the various constituents of each biological sample loaded onto the gel to migrate in a diffential manner. This pair of electrodes being constituted by an electrode connected to the negative pole of a generator and, for example, situated at the edge of the porous membrane opposite to that which is joined to the projecting elements and a positive electrode connected to the positive pole of a generator, situated at the end of the electrophoretic slab support opposite to that in the vicinity of which the biological samples are loaded.

In this embodiment of the invention, the fastest moving molecules migrate first and, in order to obtain a representative analysis, it is necessary to transfer to the gel the entire biological sample loaded on the projecting elements.

The use of such a device may be advantageous when working with dilute samples.

In this case, when all of the substances contained in the sample have migrated from the porous material onto the gel, the electrophoresis has already started, the application is interrupted and the negative pole of the generator is connected to the end of the electrophoretic support in the vicinity which the biological samples were loaded and the electrophoresis is then continued in the usual way.

The invention relates to an apparatus in which each projecting element is fitted with means which prevent a biological sample, loaded in the proximity of the upper transverse section of the said projecting element, from spreading over its surface. These means are advantageously constituted by a surface made of a hydrophobic material, such as a strip preferably attached to at least a part of the surface of the projecting elements which is opposite to the surface, a part at least of which is maintained by the stiffening support. The surface area of this hydrophobic material may vary advantageously from about one fifth to approximately the whole of one of the two surfaces of the projecting element.

Figure 6A:
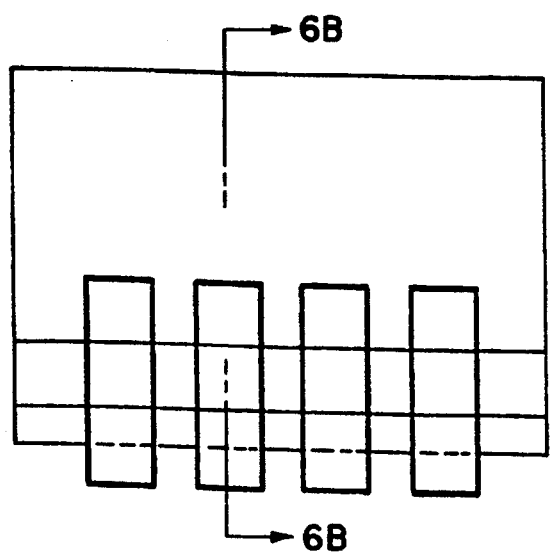
Figure 6B:
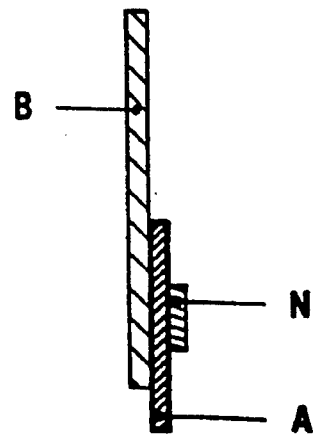

In yet another embodiment of the present apparatus a strip of hydrophobic material (FIG. 6(N)) is applied in the median part of the porous membrane (FIG. 6(A)) which apparatus comprises a porous membrane having at least one projecting element (FIG. 6(A)) attached to a solid support (FIG. 6(B)).

In the case of a strip, there is retention of the biological sample.

More precisely, the projecting elements are cut in the form of squares or rectangles and are attached to a rigid support, for example by gluing. A strip (for example a hydrophobic self-adhesive paper) is placed on the central part of the projecting elements. It plays the role of a barrier between the lower part and the upper part of each element of the porous membrane.

The sample is deposited in excess on the porous membrane, for example by means of a pipette in proximity to the upper transverse section or on the upper transverse section of the projecting element, above the strip. This strip placed on the surface of the porous membrane will prevent the sample from spreading over the surface of the projecting element, but will not prevent it from diffusing, by means of capillary action to the interior of the projecting element and reaching the lower end.

The sample having been loaded in excess with respect to the saturation of the porous membrane, the sample drop remaining above the strip will play the role of reserve humidification liquid.

The above-mentioned apparatus depisted in FIG. 6 is effective when the porous membrane has a relatively small size, i.e. less than about $3\mu$.

In the case of a porous membrane having a large pore size (larger than about $3\mu$, even larger than about $5\mu$), the apparatus mentioned above cannot function.

In fact, when the size of the pores is large and if the humidification liquid is not sufficiently viscous, the liquid siphons through the pores resulting in a liquid transfer when the samples are applied to the gel resulting in non-focused loads.

In the case of a pore size greater than about $3\mu$, the invention offers an apparatus in which each projecting element is fitted with means which prevent a biological sample, loaded at the proximity of the upper transverse section of the said projecting element, from spreading over its surface and seeping out over its surface, these means being advantageously constituted by a hydrophobic material, coating the two surfaces of the projecting element (as well as the longitudinal sections, if necessary), to the exclusion of the two transverse sections. This hydrophobic material is advantageously coated to the extent of from about 20% to about 100% on the two surfaces upwards from their lower transverse section, in particular to the extent of 100% of the surface maintained by the stiffening support and about 20% to 100% of the surface opposite to this surface, and coating in particular the whole of the two above-mentioned surfaces with the exclusion of the two transverse sections.

Figure 7B:
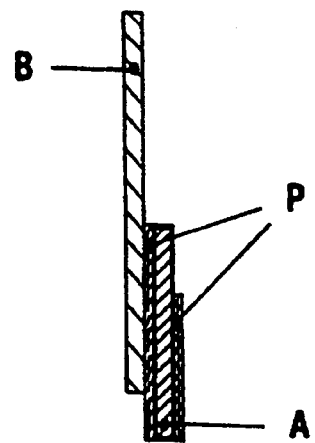

In yet another embodiment, a hydrophobic coating (FIG. 7(P)) can also be applied to the porous membrane containing at least one the projecting element on one side of the solid support (FIG. 7(B)) and the opposite side with the exception of the transverse sections as depicted in FIG. 7.

In the case in which one of the surfaces is only coated partially by the hydrophobic material, in particular the surface opposed to that maintained by the stiffening support, it is necessary that the zone in proximity to the lower transverse section be coated with a hydrophobic material in order to prevent seeping out. That is the reason why it is essential to specify that the coating of the two surfaces, when it is partial, occurs upwards from the lower transverse section.

Each projecting element (of high porosity) is film coated on its two surfaces with a hydrophobic coating, except for the two transverse sections.

In the case of a hydrophobic coating, there is retention and partitioning of the biological sample. The projecting elements are attached, at least in part, for example by gluing, to stiffening agents, such as a stiffening support.

In other words, the projecting elements are, in the proximity of the lower transverse section, coated with a hydrophobic film and are hence impermeable to the water which can cover the whole of the projecting element with the exception of the two transverse sections, and possibly with the exception of a part of the surface opposite to that maintained by the stiffening support provided that this uncoated zone is not joined to the lower transverse section, in order to avoid the biological sample from seeping out.

The sample is loaded in excess, for example by means of a pipette, on the uncoated zone, advantageously on the upper transverse section. The sample diffuses by capillary action into the projecting element at the interior of the hydrophobic coating until it reaches the end of the projecting element which, not being film-coated on its lower transverse section, makes loading the sample possing when it is applied to the gel possible.

The fact of having coated the surface of each projecting element with a hydrophobic film (from several microns to several tens of microns thick, and advantageously about 5μ to about 30μ thick) prevents the liquid from seeping out transversely by siphoning from the interior of the projecting element towards its surface, which would lead to an accumulation of sample liquid at its surface which would then run along this surface until it reaches the end of the projecting element to give a large unfocused load.

By making each projecting element impermeable, the only movement of the sample liquid is a longitudinal movement, which occurs very slowly, given the large distance to be covered and the considerable loss of load at the pores, whereas the transverse movement of liquid exudation which occurs in the absence of waterproofing takes place much more readily (short distance to be covered since the porous membrane is very thin: 50 to 200μ).

Furthermore, in the absence of waterproofing, the result of the exudation phenomenon is amplified at the end of each projecting element, since all of the liquid which has seeped out transversely accumulates there by gravity.

This hydrophobic coating may be produced by spraying or coating or forming a film on each projecting element when hydrophobic substances such as silicone, paraffin, polytetrafluoroethylene, latex, a plastic such as polyethylene, or any coating making it possible to waterproof the surface of the porous membrane without penetrating into it while adhering to it.

When the apparatus of FIG. 6 comprises independent projecting elements, the loading volume of a biological sample onto a projecting element is about $6 \times 10^{-4}$ to $27 \times 10^{-4}$ $\mu L/mm^2$ per $\mu$ of thickness of the porous material, for a degree of porosity of about 50% to about 90%.

The invention also relates to an apparatus in which each projecting element possesses a length of contact with the gel of about 1 mm to about 200 mm, and preferably from about 1 mm to about 40 mm, depending on which biological sample is loaded onto the gel.

The invention also relates to an apparatus according to which the porous membrane and/or the projecting elements are composed of a hydrophobic material containing a wetting agent of the type and in an amount such that it does not denature the components contained in the sample to be analyzed; this wetting agent being in an amount such that the sample can be loaded in sufficient quantity on one of the projecting elements and in an amount lower than that at which the biological sample can no longer be concentrated at the extremity of the projecting element. The wetting agent is advantageously glycerol, 1,3-butanediol or uncharged surfactants such as Triton X-100 ®, Tween ® advantageously used at concentrations from about 0.001% to about 10%.

The invention relates to a procedure for loading one or more biological samples onto an electrophoretic slab support, in particular an electrophoresis gel, characterized in that biological samples are loaded onto one and advantageously several projecting elements in particular, at the free end of the said projecting elements. These projecting elements being such that they all have at least one point capable of being placed in contact with the planar surface of the said electrophoretic slab support. These different points being capable of being simultaneously placed in contact with the surface of the said slab support as a result of an alignment, when the above-mentioned porous membrane is arranged in an inclined or perpendicular plane with respect to the surface of the above-mentioned slab support. FIGS. 1 to 5, 8, 9 and 10 illustrate the various apparatuses that can be used in this procedure.

If necessary, at least a part of the above-mentioned porous membrane is attached to the stiffening devices, in particular a stiffening support.

It is preferable to avoid the diffusion of the biological samples from the end of the projecting elements towards the porous membrane with the aid of means for humidification of the projecting elements, these humidification means comprising a humidification liquid which, as a consequence of evaporation of liquid from the biological sample, creates a flux from the porous membrane towards the end of the projecting elements and forces the biological samples towards the free end of the projecting elements, and which concentrates the biological sample at this end, these humidification means being described above.

The projecting elements of the porous membrane, a part of which is possibly attached to a stiffening support are placed in contact with the electrophoretic slab support in order to cause diffusion of the sample from the projecting elements onto the electrophoretic slab support and to thus load the sample onto the slab support.

The humidification, when it is done, must be sufficient so that the whole of the surface of the porous membrane and the surface of the projecting elements free of the biological sample are saturated with humidification liquid.

The diffusion of the samples from the ends of the projecting elements towards the porous membrane is prevented before or after attachment of part of the projecting elements of the porous membrane to a stiffening support.

When humidification is performed before the loading of the biological sample, it is necessary that part of the ends of the projecting elements designed to receive the biological samples is not saturated with humidification liquid in order for it to be possible to load the biological sample.

According to another embodiment of the procedure of the invention, the diffusion of the biological samples and their concentration towards the end of the projecting elements is caused by creating a flux of humidification liquid towards the end of the projecting elements on which the biological samples are loaded; for example by evaporation of the liquid of the biological sample or by accelerating this evaporation and the flux, for example by ventilation in a current of air at a temperature less than or equal to 40° C.

According to another process embodiment of the invention, the loading of the biological samples onto the electrophoretic slab support is done while an electric current is applied to the porous membrane and the projecting elements. The humidification liquid in this case is a buffer solution at a pH such that all of the molecular species of the sample to be analyzed are ionized and acquire a charge of the same sign. This charge is negative if the pH is one unit higher than the isoelectric point of the most basic molecular species, or positive if the pH is one unit lower than the isoelectric point of the most acidic molecular species, by the intermediary. The apparatus used in this process is also described above.

Generally speaking, in the case where it is desired to determine proteins in sera, advantageously a pH of about 10 to 10.5 will be selected, i.e., a pH value higher than the highest isoelectric point.

In order to confer a negative charge on the molecular species, it is possible to use a Tris-HCl, glycinate or carbonate-bicarbonate buffer, etc . . .

In order to confer a positive charge on the molecular species, it is possible to use an acetic acid-acetate, citric acid-citrate buffer, etc . . .

The invention also relates to a procedure for loading of one or more biological samples onto an electrophoretic slab support, characterized in that biological samples are loaded onto one or advantageously several planar elements, made of porous material, independent of each other and attached to common stiffening devices, in particular a stiffening support. The stiffening support maintains the above-mentioned elements in the same plane. These elements project beyond the stiffening devices, and are designated hereafter as "projecting elements". These projecting elements possessing two surfaces, one of which is at least in part supported by the stiffening devices and the other surface is the reverse of the one previously defined; two longitudinal sections; and two ends corresponding approximately to transverse sections, one of these sections being designed to be applied to the electrophoretic slab support and being designated as "lower transversal section" (close to the lower end) and a transverse section opposite to that previously defined and designated as "upper transverse section" (in the vicinity of the upper end).

The stiffening devices being such that their form and their dimensions are compatible with those of the projecting elements, to support of a part of the projecting elements by the stiffening devices under conditions such that the stiffening devices do not hinder the placing in contact of the projecting elements with the planar surface of the electrophoretic slab support and the loading of the biological sample on the electrophoretic slab support.

Each of said elements described above comprising means which prevent a biological sample loaded onto one of the projecting elements to spread over the surface of the said projecting elements, and/or to seep over the surface of the said projecting element. These projecting elements have at least one point capable of being placed in contact with the surface of the chromatographic support. These different points are capable of being placed simultaneously in contact with the surface of the said support as a result of an alignment when the above-mentioned stiffening devices are arranged in an inclined or perpendicular plane with respect to the surface of the slab support.

The projecting elements attached to the stiffening support are placed in contact with the electrophoretic slab support so that the sample can diffuse from the projecting elements onto the electrophoretic slab support and thus be loaded onto the said slab support.

The invention also relates to a procedure using an apparatus of the invention in which one of the two above-mentioned surfaces of each projecting element is fitted with a strip placed in the vicinity of the central part of the projecting element as described above in FIG. 6.

When using this apparatus depicted in FIG. 6 the biological sample is loaded in excess onto the upper part of the projecting element, in particular in the vicinity of the upper transverse section. The biological sample thus loaded does not spread over the surface of the projecting element but diffuses to the interior of the projecting element and reaches the lower transverse section of the said projecting element in order to be loaded onto the electrophoretic slab support.

In this case, the biological sample may be concentrated by evaporation in air of a part of the liquid of the biological sample.

The invention also relates to a procedure using an apparatus of the invention in which each projecting element is coated with a hydrophobic material on both of its surfaces, as described above and depicted in FIG. 7. This hydrophobic material coats about 20% to about 100% of the two surfaces upwards from their lower transverse section, in particular to an extent of 100% of the surface supported by the stiffening support and from about 20% to about 100% of the reverse surface, possibly including the two longitudinal sections. In particular, the hydrophobic material is coated on the whole of the two surfaces with the exception of the two transverse sections.

When using the apparatus depicted in FIG. 7 a biological sample is loaded in excess onto an area of the projecting element not coated with a hydrophobic material, advantageously in the vicinity of the upper transverse section. Since the sample diffuses longitudinally into the interior of the hydrophobic film until it reaches the lower transverse section of the projecting element which is not coated, the loading of the biological sample onto the electrophoretic slab support is achieved by means of capillary action.

In this particular arrangement, it is not possible to concentrate the sample by evaporation which was possible in the case of a porous membrane joined to the projecting elements as indicated previously, in view of the fact that the sample situated close to the end of each projecting element is protected from evaporation (only the transverse section of the end is exposed to the air). In order to load variable amounts of sample, the only parameter which can be varied is the time of application to the gel.

The invention also relates to a loading procedure not followed by electrophoretic migration, such as the "cross-dot" procedure or an immunofixation procedure.

In the case of a cross-dot, the procedure is as follows:
loading of a biological sample onto a slab support with the aid of projecting elements is performed in conformity with what has already been described, this loading not being followed by electrophoresis;
then, in an approximately perpendicular direction, loading of a reactive at right angles to the above load is carried out;
incubation is allowed to proceed; and
the result of the reaction possibly formed between the biological sample and the reagent is revealed.

In the case of immunofixation, the procedure is as follows:
a biological sample is loaded as indicated above;
electrophoretic migration is allowed to occur;
and when the migration is complete, a reagent is loaded in a direction approximately perpendicular to the first load over a distance encompassing the entire electrophoretic migration;
incubation is allowed to proceed; and
then the result of the reaction possibly formed between the biological sample and the reagent is revealed.

The invention is illustrated by the examples below which are in no way limiting and which make reference to the figures which, for reasons of simplification, show four projecting elements, it being understood that the apparatuses used in the examples, when they make reference to a particular figure, may in actual fact possess a number of projecting elements different from four (for example one, six or eight).

EXAMPLE 1

PROTEIN ANALYSIS OF A SERUM INVOLVING STAINING WITH PONCEAU RED

A porous membrane of cellulose acetate having pore dimensions of $8\mu$ and a thickness of $140\mu$ is used, which comprises six projecting elements 4.0 mm in diameter and separated from each other by 2 mm. This membrane is attached to a rigid support (in conformity with the diagram shown in FIG. 1).

1 $\mu$l of pure serum is loaded by means of a micropipette onto each projecting element close to its end.

The reservoir (D) constituted by parts preglued to the porous membrane (A) is then loaded by means of a pipette with 400 $\mu$l of humidification liquid consisting of a 0.5% aqueous solution of polyacrylamide of molecular mass $5 \times 10^6$.

After exposure to air for 5 minutes, the apparatus is applied for one minute to a gel intended for the analysis of proteins.

After migration, the gel is fixed, dried and stained with Ponceau red according to the usual procedures.

EXAMPLE 2

PROTEIN ANALYSIS OF A SERUM INVOLVING STAINING WITH AMIDO BLACK

The procedure is the same as indicated in example 1, except that the exposure time is reduced to two minutes and the application time to 30 seconds.

After migration, the gel is fixed, dried and stained with Amido Black according to the usual procedures.

EXAMPLE 3

PROTEIN ANALYSIS OF A SERUM INVOLVING STAINING WITH ACID VIOLET

The procedure is the same as indicated in example 1, except that the exposure time is reduced to two minutes and the application time to fifteen seconds.

After migration, the gel is fixed, dried and stained with Acid Violet according to the usual procedures.

EXAMPLE 4

HIGH RESOLUTION PROTEIN ANALYSIS OF A SERUM

A porous membrane of cellulose acetate, having pore dimensions of $1.2\mu$ and a thickness of $100\mu$, is used which comprises four projecting elements 7 mm in diameter and separated from each other by 3 mm, this membrane being attached to a rigid support (cf. Figure 5).

By means of a micropipette, one drop of 5 $\mu$l of each of four samples to be analysed by 10 mm from each other are loaded onto parafilm in a straight line.

The free ends of the projecting elements are simultaneously placed in contact with the various samples until the front of the liquid samples has been absorbed into the projecting elements to a height of 3 mm from the end.

The spongy material is then impregnated with 1 ml of humidification liquid consisting of a 10% aqueous solution of Dextran of molecular mass $5 \times 10^5$ by means of a pipette.

After a waiting period of 5 minutes the apparatus is applied for 30 seconds to a gel intended for high resolution analysis of proteins.

After migration, fixation and drying, the gel is stained with Acid Violet according to the usual procedures.

EXAMPLE 5
PROTEIN ANALYSIS OF A SERUM INVOLVING STAINING WITH AMIDO BLACK

A porous membrane of cellulose acetate, having a pore size of $0.45\mu$, a thickness of $130\mu$ and impregnated with 2% of 1,3-butanediol, is used which comprises eight projecting elements 3 mm in diameter separated from each other by 1.5 mm, and attached to a rigid support (in conformity with the diagram shown in FIG. 2).

By means of a micropipette, 1 $\mu$l of each sample is loaded close to the end of each projecting element. The reservoir (D) constituted by the rigid support (B), and by the porous membrane (A), is loaded with 200 $\mu$l of physiological water.

After exposure to air for 2 minutes the apparatus is applied for 1 minute to a gel intended for the analysis of proteins.

After migration, the gel is fixed in a stream of air heated to 70° C. and stained with Amido Black according to the usual procedures.

EXAMPLE 6
PROTEIN ANALYSIS OF A SERUM INVOLVING STAINING WITH PONCEAU RED

A porous membrane of nylon, having a pore size of $0.45\mu$ and a thickness of $120\mu$, is used which comprises six projecting elements 4 mm in diameter and separated from each other by 2 mm, this membrane is supported on a stiffening support (in conformity with the diagram shown in FIG. 4).

By means of a micropipette, $1\mu$ of each sample is loaded close to the end of each projecting element.

The reservoir (D), constituted by the elements (B) and (C) of the rigid support, and by the flexible magnetic elements (J) and (H), is loaded with 100 $\mu$l of water by means of a pipette.

The entire apparatus and, in particular, the ends of the projecting elements extending beyond the stiffening system, is placed for 2 minutes in a current of air at room temperature before being applied for 1 minute to an agarose gel intended for the separation of proteins.

After migration, the gel is fixed, dried and stained with Ponceau red according to the usual procedures.

EXAMPLE 7
LIPID ANALYSIS OF A SERUM ON AGAROSE GEL: STAINING WITH SUDAN BLACK

A porous membrane of cellulose acetate, having a pore size of $8\mu$ and a thickness of $140\mu$, is used which comprises six projecting elements 4 mm in diameter separated from each other by 2 mm, this membrane is attached to a stiffening support (in conformity with the diagram shown in FIG. 3).

By means of a micropipette, 1 $\mu$l of each sample is loaded close to the ends of the projecting elements.

The reservoir, constituted by the rigid support (D), and the flexible flap (F), inclined at about 45°, is loaded by means of a pipette with 100 $\mu$l of humidification liquid constituted by a 1% solution of hydroxyethyl cellulose of molecular weight $5 \times 10^5$.

After exposure to air for 10 minutes, the apparatus is applied for 2 minutes to a gel intended for the separation of lipoproteins.

After being dried in a stream of warm air, the gel is stained with Sudan Black according to the usual procedures.

EXAMPLE 8
ANALYSIS OF THE ISOENZYMES OF LACTATE DEHYDROGENASE (LDH)

The procedure is as indicated in example 6, except that the time of exposure is reduced to 6 minutes.

The apparatus is then applied for 2 minutes to an agarose gel intended for the separation of the isoenzymes of the LDH.

After migration, the gel is immediately stained by means of the usual substrates according to standard procedures.

EXAMPLE 9
DETECTION AND IDENTIFICATION OF THE PARAPROTEINS BY IMMUNOFIXATION

A porous membrane of cellulose acetate, having a pore size of $8\mu$ and a thickness of $140\mu$, is used which comprises a single projecting element 40 mm in diameter attached to a stiffening support (in conformity with the diagram shown in FIG. 3).

By means of a micropipette, and close to the end of the projecting element and along the entire length of this element, is deposited the sample previously diluted 1/5 in physiological water so that it spreads to a height of about 5 mm measured from the end of the projecting element.

The reservoir, constituted by the rigid support (B) and the flexible flap (F) inclined at about 45°, is loaded with 100 $\mu$l of humidification liquid constituted of a 0.25% aqueous solution of polyacrylamide of molecular mass $5 \times 10^6$.

After a waiting period of 2 minutes, the apparatus is applied for 30 seconds to a gel intended for immunofixation analyses.

After migration, the gel is treated according to the usual procedures of immunofixation.

EXAMPLE 10
DETECTION AND IDENTIFICATION OF THE PARAPROTEINS BY IMMUNOFIXATION

The procedure is as indicated in example 8, up to the end of the migration step.

The loading of the antisera performed previously with a mask is replaced by loadings carried out by means of the same approach as that used for the loading of the sample, namely five porous membranes of cellulose acetate, having a pore size of 8μ and a thickness of 140μ, are used, each of which comprises a single projecting element 40 mm in diameter, which is attached to a stiffening support (in conformity with the diagram shown in FIG. 3).

By means of a micropipette, each of the anti-IgG, anti-IgA, anti-IgM, anti-kappa and anti-lambda antisera are loaded onto each of the five porous membranes close to the ends of the projecting elements and over a height of about 5 mm.

Each of the five reservoirs is loaded with 100 μl of humidification liquid constituted by a 0.25% solution of polyacrylamide of molecular mass $5\times10^6$.

After a waiting period of 2 minutes the five porous membranes are simultaneously applied (for 2 minutes), perpendicularly to the initial loading of the sample and at 5 mm from each other.

Incubation is allowed to proceed for 10 minutes and the remainder of the procedure is performed according to the usual techniques.

EXAMPLE 11

ANALYSIS OF THE PROTEINS IN A URINE

A porous membrane of cellulose acetate, having a pore size of 8μ and a thickness of 140μ, is used which comprises four projecting elements 6 mm in diameter separated from each other by 3 mm, and the membrane is attached to a stiffening support (cf. FIG. 5).

By means of a micropipette, 6 μl of sample are loaded close to the end of each projecting element, the front of the sample being at a distance of about 7 mm from the ends of the projecting elements.

The humidification liquid is supplied by a 1% agarose gel 1 mm thick (cf. FIG. 5, part (L) containing a 0.05 M sodium bicarbonate carbonate buffer, pH 10.5).

The entire apparatus, and in particular the ends of the projecting elements extending beyond the stiffening system, is placed in a current of air for 3 minutes at room temperature, the time necessary for the sample front to become situated at 0.5 mm from the end of the projecting elements.

The upper end of the element L (agarose gel) is then connected to the positive pole of a generator, and the positive pole of the generator is connected to the bottom of the electrophoresis gel, the end furthest away from the side of application.

The application to an agarose-7% acrylamide gel is performed at a voltage of 300 V for 1 minute.

After the application, the end of the electrophoresis gel situated close to the side of application (the top) is connected to the negative pole of the generator and migration is allowed to continue.

After migration, the gel is stained with Coomassie Blue according to the usual procedures.

EXAMPLE 12

PROTEIN ANALYSIS OF A SERUM INVOLVING STAINING WITH ACID VIOLET

An apparatus of the invention is used which comprises four independent projecting elements made of a porous material (cellulose acetate), having pore dimensions of 1.2μ and a thickness of 100μ, these projecting elements being rectangular, 12 mm high and 7 mm wide, separated from each other by 2 mm and glued to a rigid support (cf. FIG. 6).

A strip of hydrophobic paper (N) is glued across the middle of the projection elements.

The entire apparatus is placed in a horizontal position and by means of a pipette 15 μl of sample are loaded per projecting element on the area of the projecting element situated above the strip (N) and remote from the end which is subsequently applied to the gel.

After a waiting period of about 1 minute, the sample has reached the end by capillary diffusion in the porous membrane.

After an additional waiting period of 2 minutes for the purpose of concentration by evaporation in air, the apparatus is applied for 20 seconds to an agarose gel intended for the analysis of proteins.

After migration, the gel is fixed, dried and stained with Acid Violet according to the usual procedures.

EXAMPLE 13

PROTEIN ANALYSIS OF A SERUM INVOLVING STAINING WITH AMIDO BLACK

A porous membrane of cellulose acetate, having pore dimensions of 8μ and a thickness of 140μ, is used.

The apparatus of the invention comprises four independent projecting elements (made of porous material), in the form of a square of size 7 mm, separated from each other by 2 mm, each projecting element being coated with a coating of a plastic film 10μ thick, except for the lower transverse section of the projecting element and for an area 3 mm high situated in the proximity of the upper transverse section (cf. FIG. 7).

The apparatus is placed in the horizontal position and by means of a pipette 12μ of sample are loaded onto the zone uncoated by the plastic coating.

After about 30 seconds, the sample liquid has reached the end of the porous elements by means of capillary action.

The apparatus is then applied for 30 seconds to an agarose gel intended for the analysis of proteins by electrophoresis.

After migration, the gel is fixed, dried and stained with Amido black according to the usual procedures.

I claim:

1. Procedure for loading of one or several biological samples on an electrophoretic slab support, comprising the steps of:
    loading the one or several biological samples onto one or more projecting elements made of porous material and joined to an edge of a planar porous membrane and as an extension in a same plane of said planar porous membrane, the loading of the one or several biological samples being performed at a free end of the one or more projecting elements, the one or more projecting elements being such that they all have at least one point capable of being placed in contact with a planar surface of the electrophoretic slab support, different points being simultaneously placed in contact with the planar surface of the electrophoretic slab support as a result of an alignment, when the planar porous membrane is arranged in an inclined or perpendicular plane with respect to the planar surface of the electrophoretic slab support, wherein at least a part of the planar porous membrane is attached to a stiffening support, wherein diffusion of the one or several biological samples from the free end of the one or more projecting elements towards the planar porous membrane is avoided with an aid of agents for humidification of the one or more projecting elements, the agents comprising a humidification liquid which, as a consequence of an evaporation of liquid from the one or several biological samples, creates a flux from the planar porous membrane towards the free end of the one or more projecting elements and forces the one or several biological samples towards the free end of the one or more projecting elements, and which concentrates the one or several biological samples at the free end, the agents comprising a spongy material attached in a removable or irremovable manner to the planar porous membrane or to the stiffening support or a reservoir attached in a removable or irremovable manner to the stiffening support; and placing in contact the one or more projecting elements of the planar porous membrane, a part of which is attached to the stiffening support with the electrophoretic slab support in order to cause diffusion of the one or several biological samples from the one or more projecting elements onto the electrophoretic slab support and to thus load the one or several biological samples onto the electrophoretic slab support.

2. Procedure according to claim 1, wherein the diffusion of the one or several biological samples from the free end of the one or more projecting elements towards the planar porous membrane is prevented before or after attachment of a part of the one or more projecting elements of the planar porous membrane to the stiffening support.

3. Procedure according to claim 2, wherein the diffusion of the one or several biological samples and concentration towards the free end of the one or more projecting elements is caused by creating a flux of humidification liquid by evaporation of the humidification liquid of the one or several biological samples, or by accelerating the evaporation and flux by a current of air at a temperature lower than or equal to 40° C.

4. Procedure for loading a biological sample comprising the steps of:

loading of a biological sample according to claim 1, onto a slab support with an aid of projecting elements, the loading not being followed by electrophoresis;

loading of a reagent in a direction perpendicular to a previous load and intersecting the previous load;

incubating said biological sample with said reagent; and revealing a result of a reaction possibly formed between the biological sample and the reagent.

5. Procedure for loading a biological sample comprising the steps of:

loading a biological sample according to claim 1, allowing an electrophoretic migration to take place;

loading a reagent in a direction approximately perpendicular to a first loading over a distance;

encompassing an entire distance of the electrophoretic migration when the electrophoretic migration is complete;

allowing incubation to proceed; and revealing a result of a reaction formed between the biological sample and the reagent.

6. Procedure for loading one or several biological samples onto an electrophoretic slab support, comprising the steps of:

loading the one or several biological samples onto one or more independent planar elements, made of porous material, attached to common stiffening devices, which maintains the one or more independent planar elements in a same plane, the one or more independent planar elements projecting beyond the common stiffening devices as projecting elements, each of the projecting elements comprising:

two surfaces, one of which is at least in part supported by the common stiffening devices wherein one of the two surfaces of each of the projecting elements is fitted with a strip placed in a vicinity of a central part of the each of the projecting elements and attached to at least a part of the surface of the each of the projecting elements which is a reverse of the surface of which a part at least is supported by the common stiffening devices, thus dividing the each of the projecting elements into an upper part and a lower part, a size of the strip varying from one fifth to a whole of one of the two surfaces of the each of the projecting elements, two longitudinal sections, two ends corresponding approximately to transverse sections, one of the transverse sections being designed to be applied to the electrophoretic slab support and being designated as a lower transversal section and the other one of the transverse sections opposite to the lower transversal section and designated as an upper transversal section, the common stiffening devices being such that form and dimensions are compatible with form and dimensions of the projecting elements, to support a part of the projecting elements by the common stiffening devices under conditions such that the common stiffening devices do not hinder placing in contact of the projecting elements with a planar surface of the electrophoretic slab support and the loading of the one or several biological samples on the electrophoretic slab support, each of the projecting elements comprising means which prevent a biological sample loaded onto one of the projecting elements to spread over the surface of the projecting elements, and/or to seep over the surface of the projecting elements, the projecting elements having at least one point of contact with the surface of the electrophoretic slab support, different points being placed simultaneously in contact with the planar surface of the electrophoretic slab support as a result of an alignment when the common stiffening devices are arranged in an inclined or perpendicular plane with respect to the planar surface of the electrophoretic slab support, and placing in contact the projecting elements attached to the common stiffening devices with the electrophoretic slab support wherein the one or several biological samples is loaded in excess onto an upper part of the projecting element in a vicinity of the upper transversal section, the one or several biological samples thus loaded does not spread over the surface of the projecting element, diffuses to an interior of the projecting element and reaches the lower transversal section of the projecting element in order to be loaded onto the electrophoretic slab support.

7. Procedure according to claim 6, wherein each projecting element is coated with a hydrophobic material on both its surfaces, and on the two longitudinal sections, the hydrophobic material being such that the hydrophobic material recovers 20% to 100% of the two surfaces upwards from the lower transversal section, to an extent of 100% of a surface supported by the stiffening devices and from 20% to 100% of a reverse surface, and hydrophobic coats a whole of the two surfaces with an exception of the two transverse sections, wherein a biological sample is loaded in excess in the vicinity of the upper transversal section of the projecting element which is not coated by the hydrophobic material, and since the biological sample diffuses longitudinally into an interior of a hydrophobic film until the biological sample reaches the lower transversal section of the projecting element which is not coated, the loading of the biological sample onto the electrophoretic slab support is achieved by capillary action.

8. An apparatus for an application of biological samples to an electrophoretic slab support, comprising:
(a) a planar porous membrane including on one of edges one or more projecting elements made of porous material said projecting elements being partially joined to said planar porous membrane and lying in a same plane as said planar porous membrane wherein a part of the projecting elements not joined to the planar porous membrane has a free end;
(b) at least one stiffening device attached to said one or more projecting elements wherein the stiffening device maintains in the same plane as said one or more projecting elements; and
(c) means for humidificating said one or more projecting elements, said humidification means being separable or inseparable from said planar porous membrane.

9. The apparatus according to claim 8, wherein said one or more projecting elements are resting on an edge of a planar porous membrane, joined to the planar porous membrane, extending in the same plane as the planar porous membrane and acting as a projection of the planar porous membrane as the one or more projecting elements wherein a projecting part of the one or more projecting elements not joined to the planar porous membrane has a full end, the planar porous membrane and the one or more projecting elements having a thickness of $50\mu$ to $200\mu$.

10. The apparatus according to claim 9, wherein said one or more projecting elements have a thickness of $100\mu$ to $150\mu$.

11. The apparatus according to claim 8, wherein said one or more projecting elements are independent of each other.

12. The apparatus according to claim 8, wherein the planar porous membrane and the one or more projecting elements are a same porous material, the one or more projecting elements being cut from one of the edges of the planar porous membrane.

13. The apparatus according to claim 12, wherein said planar porous membrane and said one or more projecting elements have a thickness of $50\mu$ to $200\mu$.

14. The apparatus according to claim 13, wherein said planar porous membrane and said one or more projecting elements have a thickness of $100\mu$ to $150\mu$.

15. The apparatus according to claim 8, wherein said one or more projecting elements are separated, square or rectangular strips.

16. The apparatus according to claim 15, wherein said strips are separated by a distance of at least 0.5 mm.

17. The apparatus according to claim 8, wherein said means for humidificating is a material impregnated with a humidification liquid.

18. The apparatus according to claim 17, wherein said material impregnated with said humidification liquid is a spongy material.

19. The apparatus according to claim 8, wherein said planar porous material is a hydrophilic material selected from a group of cellulose, a cellulose ester, cellulose acetate, cellulose proprionate, cellulose nitrate, mixed esters of cellulose nylon and derivatives thereof.

20. The apparatus according to claim 8, wherein said planar porous material is a hydrophobic material selected from a group of polyethylene, polypropylene, polycarbonate and derivatives thereof.

21. The apparatus according to claim 8, wherein said means for humidificating is a reservoir integrated into said stiffening device or detachable from said stiffening device.

22. The apparatus according to claim 8, wherein said planar porous membrane is a sheet of cellulose acetate, rectangular or square and the one or more projecting elements are strips separated from each other and situated on one side of the planar porous membrane.

23. The apparatus according to claim 8, wherein said planar porous membrane is a sheet of paper and the one or more projecting elements are separated from each other and situated on one side of the planar porous membrane.

24. The apparatus according to claim 8, wherein attached to at least part of the surface of each of the one or more projecting element is a hydrophobic material.

25. The apparatus according to claim 24, wherein said hydrophobic material further contains a wetting agent of glycerol, 1,3-butane dial or uncharged surfactants at concentrations from 0.001% to 10%.

* * * * *